US012805506B2

(12) United States Patent
Chojnacki et al.

(10) Patent No.: US 12,805,506 B2
(45) Date of Patent: Nov. 24, 2026

(54) LINKABLE INSECT REPELLER STATION AND CONTROL SYSTEM

(71) Applicant: Thermacell Repellents, Inc., Bedford, MA (US)

(72) Inventors: Adam Chojnacki, Bedford, MA (US); Robert G. Holmes, Jr., Bedford, MA (US); Steven M. Bourque, Bedford, MA (US); Justin Michael Thomas, Bedford, MA (US)

(73) Assignee: Thermacell Repellents, Inc., Bedford, MA (US)

(*) Notice: Subject to any disclaimer, the term of this patent is extended or adjusted under 35 U.S.C. 154(b) by 881 days.

(21) Appl. No.: 18/021,038

(22) PCT Filed: Aug. 12, 2021

(86) PCT No.: PCT/US2021/045760
§ 371 (c)(1),
(2) Date: Feb. 13, 2023

(87) PCT Pub. No.: WO2022/036107
PCT Pub. Date: Feb. 17, 2022

(65) Prior Publication Data

US 2023/0292729 A1 Sep. 21, 2023

Related U.S. Application Data

(60) Provisional application No. 63/222,256, filed on Jul. 15, 2021, provisional application No. 63/064,995,
(Continued)

(51) Int. Cl.

| | |
|---|---|
| ***A01M 1/20*** | (2006.01) |
| ***A01M 29/12*** | (2011.01) |
| *A61L 9/03* | (2006.01) |

(52) U.S. Cl.
CPC ........ *A01M 1/2077* (2013.01); *A01M 1/2072* (2013.01); *A01M 29/12* (2013.01); *A61L 9/03* (2013.01)

(58) Field of Classification Search
None
See application file for complete search history.

(56) References Cited

U.S. PATENT DOCUMENTS

2005/0181002 A1 8/2005 Davis et al.
2006/0022064 A1* 2/2006 Triplett ............... A01M 1/2044 239/44

(Continued)

FOREIGN PATENT DOCUMENTS

CN 205284776 U 6/2016
EP 0420144 B1 4/1994

OTHER PUBLICATIONS

EP21856723.8, European Regional phase of PCT/US2021045760; Supplementary Search Report dated Aug. 22, 2024.

(Continued)

*Primary Examiner* — John J Norton
(74) *Attorney, Agent, or Firm* — MacMillan, Sobanski & Todd, LLC

(57) ABSTRACT

An insect repeller system for installation as a fixed base unit or a plurality of linked units includes a repeller station and a mounting structure. A hub controller provides power for operation of the stations and command instructions to control the operation of the repeller station for emission of vaporized repellent fluid and/or lighting of the units.

9 Claims, 19 Drawing Sheets

Related U.S. Application Data filed on Aug. 13, 2020, provisional application No. 63/064,750, filed on Aug. 12, 2020.

(56) References Cited

U.S. PATENT DOCUMENTS

| | | | | |
|---|---|---|---|---|
| 2008/0197213 | A1* | 8/2008 | Flashinski | B05B 17/0684 239/288.5 |
| 2008/0315005 | A1* | 12/2008 | Michaels | A61L 9/14 239/4 |
| 2009/0261180 | A1 | 10/2009 | Donoho et al. | |
| 2011/0139894 | A1 | 6/2011 | Masterson et al. | |
| 2011/0253801 | A1 | 10/2011 | Buschmann | |
| 2014/0037273 | A1* | 2/2014 | Jaworski | A61L 9/037 392/390 |
| 2017/0315804 | A1 | 11/2017 | Frudakis et al. | |
| 2018/0027797 | A1 | 2/2018 | Wang | |
| 2018/0104371 | A1 | 4/2018 | Hasenoehrl | |
| 2019/0008137 | A1 | 1/2019 | Shapiro et al. | |
| 2019/0281810 | A1 | 9/2019 | Sinur et al. | |
| 2021/0086220 | A1* | 3/2021 | Hasik | A01M 1/2044 |

OTHER PUBLICATIONS

PCT/US2021/045760; Int'l Search Report and Written Opinion dated Jan. 10, 2022.
CN205284776U English Machine Translation provided with PCT Search Report dated Jan. 10, 2022.

* cited by examiner

LINKABLE INSECT REPELLER STATION AND CONTROL SYSTEM

CROSS-REFERENCE TO RELATED APPLICATIONS

This application claims the benefit of U.S. Provisional Application No. 63/064,750, filed Aug. 12, 2020; U.S. Provisional Application No. 63/064,995, filed Aug. 13, 2020; and U.S. Provisional Application No. 63/222,256, filed Jul. 15, 2021. The disclosures of these applications are incorporated herein by reference in their entirety.

BACKGROUND OF THE INVENTION

This invention relates in general to insect repeller devices. In particular, this invention relates to an insect repeller device that is linkable to other insect repeller devices and a control unit to regulate the emission of volatile material to control insects and/or create a pleasant outdoor environment within a defined area.

Outdoor spaces provide an attractive place for people to gather, eat, and relax. However, these spaces also attract insects and other pests which can hamper effective area utilization and, particularly in a commercial setting, create an undesirable environment which reduces profitability and adversely can impact a facility's reputation. Individual repeller devices are known and create defined areas of protection from pests. These devices work well but are independently operated and may not provide efficient utilization of volatized materials which increases costs. Other devices are known to be linked to provide power for heating elements but do not regulate operation of the devices in response to environmental conditions or system performance levels.

The ability to conveniently and effectively control an outdoor environment with respect to pest repelling or ambiance creation is hampered by the ability of repeller devices to communicate and coordinate operational status, adjust output parameters based on local conditions, and accommodate different materials and outputs to provide different environmental effects such as scent regulation, lighting control, and audio outputs. In addition, the outdoor environment provides deleterious conditions, such as rain, wind, and temperature changes that reduce the ability to efficiently use emissive materials. Thus it would be desirable to provide an outdoor environmental control system that provides the ability to reduce pest presence, provides a pleasant sensory atmosphere, and is resistant to negative environmental factors that affect operation of the devices.

SUMMARY OF THE INVENTION

This invention relates in general to insect repeller devices. In particular, this invention relates to an insect repeller device that is linkable to other insect repeller devices and a control unit to control insects within a defined area. The insect repeller station may operate as a singular unit or as a series of stations placed in selected areas. In one embodiment, the station or stations are powered and operated by a separate hub control unit. The stations may also be powered individually, for example by solar, battery, or plug-in power sources. The hub controller may be a separate unit or may be incorporated into one or more of the repeller stations. The control unit operates the repeller or repellers to emit repellent material, either by natural convection or by forced convection, and may determine the duration of repellent material emission based on one or more inputs.

The linked repeller stations are in communication with the hub controller such that the amount of emitted insect repellent is matched to an insect load or pressure determination. The one or more inputs may be measured in proximity to the station installation area or may be generated from a web-based analysis of the installation area by way of weather, satellite, and/or topographical inputs that may be remotely determined. The repeller stations may be capable of emitting insect or other pest repellent material into the air, emitting fragrance materials, generating light outputs that are indicative of operational status and/or provide area lighting such as for walkways or ambiance, and may provide audio outputs. The stations may be in communication together through wired connections or wirelessly and the outputs may controlled remotely or through a controller unit.

An insect repeller system includes at least one insect repeller station having a heating element and a volatilizable insect repellent material. The at least one insect repeller station defines an upper section, a lower section, and an interface therebetween. The interface forms at least one inlet opening to draw air into the upper section, and the upper section forms an outlet opening to dispense air and the volatilizable insect repellent material. The upper section defines a diameter and a separation distance between the inlet opening and the outlet opening. The heating element is positioned within the separation distance such that a temperature differential is created within the upper section. In certain embodiments of the system, a hub controller is in communication with the at least one insect repeller station to provide at least one of input power to the at least one repeller station or command signals to control the heating element and output of the volatilizable insect repellent material for the at least one repeller station. The hub controller may be a separate unit in communication with the at least one insect repeller station or may be integrated into the at least one repeller station.

The insect repeller system of the invention includes a temperature sensor positioned proximate to the heating element, and the hub controller includes a closed loop control algorithm to operate the heating element based on output of the temperature sensor. In the closed loop control system, a plurality of insect repeller stations are each controlled individually by the hub controller.

An insect repeller system includes at least one insect repeller station having a heating element and a volatilizable insect repellent material. The at least one insect repeller station defines an upper section, a lower section, and an interface therebetween. The interface forms at least one inlet opening to draw air into the upper section, and the upper section forms an outlet opening to dispense air and the volatilizable insect repellent material. The upper section defines a diameter and a separation distance between the inlet opening and the outlet opening. The at least one inlet opening defines an air inlet cross-section of in a range of about 300-400 $mm^2$, the outlet opening defines an air/volatilizable insect repellent material outlet cross section in a range of about 2450-2650 $mm^2$, and the separation distance in a range of about 95-115 mm. The heating element is in a range of about 100-120 mm above the at least one inlet opening. In certain aspects of the insect repeller stations, some may be configured where the diameter of the upper section is a first inner diameter and a second inner diameter where the first inner diameter is smaller than the second inner diameter defining a taper over the separation distance of the upper section.

An insect repeller system includes at least one insect repeller station having a heating element and a volatilizable insect repellent material. The at least one insect repeller station defines an upper section, a lower section, and an interface therebetween. The interface forms at least one inlet opening to draw air into the upper section, and the upper section forms an outlet opening to dispense air and the volatilizable insect repellent material. The upper section defines a diameter and a separation distance between the inlet opening and the outlet opening. The heating element is positioned within the separation distance such that a temperature differential is created within the upper section. In certain embodiments of the system, the upper section includes a low specific heat material insulating the upper section over the separation distance. in other embodiments, the upper section is formed from a high specific heat material and a low specific heat material lines an inner surface of the upper section. In one aspect, the low specific heat material increases a temperature gradient over the separation distance.

An insect repeller station includes a housing defining a volume and a heating assembly including a heating element having an aperture is disposed within the volume. A fluid reservoir is supported by the heating assembly and contains a volatilizable insect repellent material. A wick extends from the volatilizable insect repellent material and into the aperture of the heating element and further emits the volatilizable insect repellent material. A recycling shield has a condensate accumulation point positioned above the wick that collects a condensate of the volatilizable insect repellent material and deposits the condensate onto the wick. In certain embodiments, the recycling shield includes a plurality of troughs defined by guides that form points arranged in a diameter larger than the heating element aperture. In certain embodiments of the recycling shield, the points collect and direct incoming water to a collection bowl and drain that permit water to pass out of the insect repeller station. In one alternative of the condensate accumulation point, it is configured as a generally hemispherical-shaped boss and the recycling shield is formed from a low specific heat material. In certain embodiments, the recycling shield is part of a cap covering one end of the housing and defining at least one outlet opening configured to dispense air and the volatilizable insect repellent material. In some embodiments, the housing forms at least one inlet opening configured to admit air into the volume. The housing forms a convective air flow through the volume and the plurality of troughs to exit though the at least one outlet. Alternatively, either the recycling shield, the cap or both components may be formed from a low specific heat material, and a gap is formed therebetween. The recycling shield may be formed from a thinner material than the cap.

An insect repeller station includes a housing defining a volume and a heating assembly including a heating element having an aperture is disposed within the volume. A fluid reservoir is supported by the heating assembly and contains a volatilizable insect repellent material. A wick extends from the volatilizable insect repellent material and into the aperture of the heating element and further emits the volatilizable insect repellent material. A recycling shield has a condensate accumulation point positioned above the wick that collects a condensate of the volatilizable insect repellent material and deposits the condensate onto the wick. The heating element is arranged at a proximal end of the housing closer to the recycling shield than a distal end of the housing. In certain embodiments, the housing is an upper section of the insect repeller station and a lower section of the insect repeller station defines an interface with the upper section forming at least one air inlet. A separation distance is defined between the upper section and the lower section such that the heating element creates a temperature differential within the volume to increase air velocity at the proximal end.

An insect repeller station includes an upper section defining an interior volume. A heating element is supported in a housing and includes an aperture. The housing extends from a support arm into the interior volume of the upper section and includes at least one bottle support structure. A fluid bottle has a bottle attachment point, a reservoir, and a wick. The bottle attachment point forms a snap fit engagement with the bottle support structure to secure the fluid bottle to the housing. A portion of the bottle support contacts the housing to align the wick through the aperture in a generally concentric orientation with the heating element. The reservoir is positioned adjacent to the support arm. In certain embodiments of the insect repeller station, the support arm is connected to a lower section and cantilevered into the interior volume. The support arm houses electrical and/or communication connections to the heating element. In yet other embodiments of the station, the bottle support structure is opposing bosses extending from the housing, and the bottle attachment point is a hood partially surrounding the wick. The hood has opposed detents that engage the attachment bosses, and the hood contacts the housing to algin the wick within the heating element. In some embodiments, the hood includes an outer attachment structure configured to interface with a bottle lid, the bottle lid configured to enclose the wick and contain fluid contents of the reservoir.

An insect repeller station includes an upper section defining an interior volume. A heating element is supported in a housing and includes an aperture. The housing extends from a support arm into the interior volume of the upper section and includes at least one bottle support structure. A fluid bottle has a bottle attachment point, a reservoir, and a wick. One of the support arm or the housing is configured to measure and report a fluid level of fluid contents of the reservoir to a controller. The measurement may be made by monitoring a bottle weight by one of a load cell, a strain gauge, or a weight scale. The controller is configured to generate a signal proportional to the fluid level.

An insect repeller station includes an upper section defining an interior volume. A heating element is supported in a housing and includes an aperture. The housing extends from a support arm into the interior volume of the upper section and includes at least one bottle support structure. A fluid bottle has a bottle attachment point, a reservoir, and a wick. In certain aspects of the invention, the hood forms a semicircular section around the wick and includes an open section that the housing passes through. In other embodiments, the fluid bottle includes reservoir cap and a bottle lid. The reservoir cap has a venting structure to prevent vacuum formation within the reservoir as fluid contents is drawn by the wick. In certain embodiments, the bottle lid forms a seal with the vent to contain the fluid contents. Alternatively, the reservoir cap may have a removable sealing means that closes the vent to contain the fluid contents.

An insect repeller system includes a plurality of insect repeller stations, where each station has a heating element and a volatilizable insect repellent material. A hub controller is in communication with each insect repeller station and provides command signals to control the heating element and output of the volatilizable insect repellent material for each station. The hub controller executes a control strategy and receives a signal from a temperature sensor indicating a heating element output temperature. The controller cycles the heating element between an on state and an off state to maintain a target temperature associated with an emission rate of the volatilizable insect repellent material.

An insect repeller system includes a plurality of insect repeller stations, where each station has a heating element and a volatilizable insect repellent material. A hub controller is in communication with each insect repeller station and provides command signals to control the heating element and output of the volatilizable insect repellent material for each station. The hub controller executes a control strategy and receives a signal from a temperature sensor indicating a heating element output temperature. The controller cycles the heating element between an on state and an off state to maintain a target temperature associated with an emission rate of the volatilizable insect repellent material. The volatilizable insect repellent material is provided as first and second volatilizable insect repellent materials associated with respective first and second repeller stations. In certain aspects, the first and second volatilizable insect repellent materials may be different. The hub controller controls the first repeller station according to the emission rate of the first volatilizable insect repellent material and controls the second repeller station according to the emission rate of the second volatilizable insect repellent material. In certain operational aspects of the invention, the hub controller controls the first insect repeller station independently of the second insect repeller station. The plurality of insect repeller stations may be further configured to self-address to the hub controller with an identifier associated with each individual repeller station of the plurality of repeller station.

An insect repeller system includes a plurality of insect repeller stations, where each station has a heating element and a volatilizable insect repellent material. A hub controller is in communication with each insect repeller station and provides command signals to control the heating element and output of the volatilizable insect repellent material for each station. The hub controller executes a control strategy and receives a signal from a temperature sensor indicating a heating element output temperature. The controller cycles the heating element between an on state and an off state to maintain a target temperature associated with an emission rate of the volatilizable insect repellent material. In certain embodiments, the temperature sensor is a negative temperature coefficient thermistor, and the hub controller is programmed with a target temperature associated with the volatilizable insect repellent material. The hub controller executes a closed-loop control operation that receives a signal from a temperature sensor indicative of a heat output of the heating element and regulates power to the heating element to operate between an upper threshold and a lower threshold associated with the target temperature.

An insect repeller system includes a plurality of insect repeller stations, where each station has a heating element and a volatilizable insect repellent material. A hub controller is in communication with each insect repeller station and provides command signals to control the heating element and output of the volatilizable insect repellent material for each station. The hub controller executes a control strategy and receives a signal from a temperature sensor indicating a heating element output temperature. The controller cycles the heating element between an on state and an off state to maintain a target temperature associated with an emission rate of the volatilizable insect repellent material. In other embodiments, the temperature sensor is a positive temperature coefficient thermistor and the hub controller is configured to operate the heating element in response to an open-loop control strategy.

Various aspects of this invention will become apparent to those skilled in the art from the following detailed description of the preferred embodiment, when read in light of the accompanying drawings.

DETAILED DESCRIPTION OF THE PREFERRED EMBODIMENT

Figure 1:
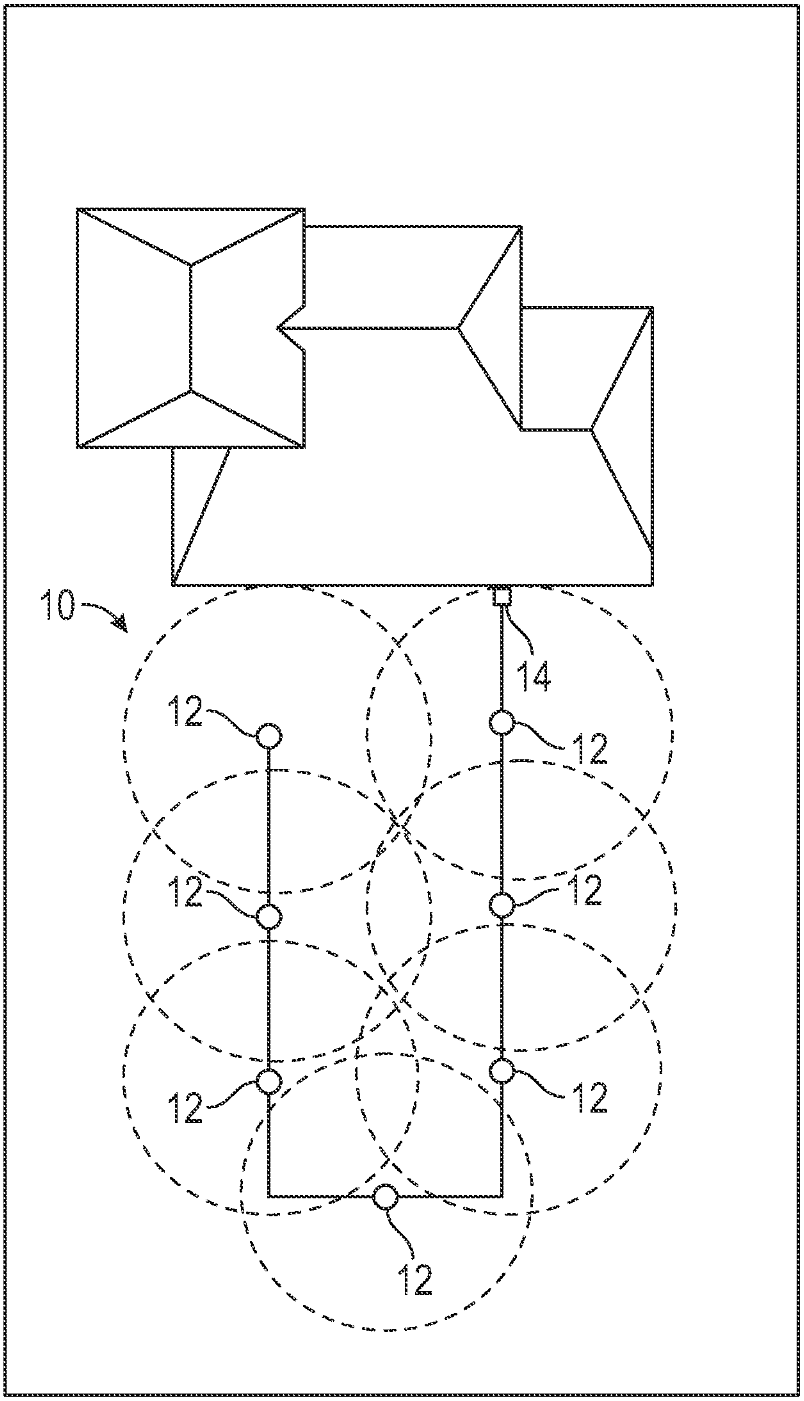
FIG. 1 is a plan view of a linked insect repeller system in accordance with the invention.
Figure 2:
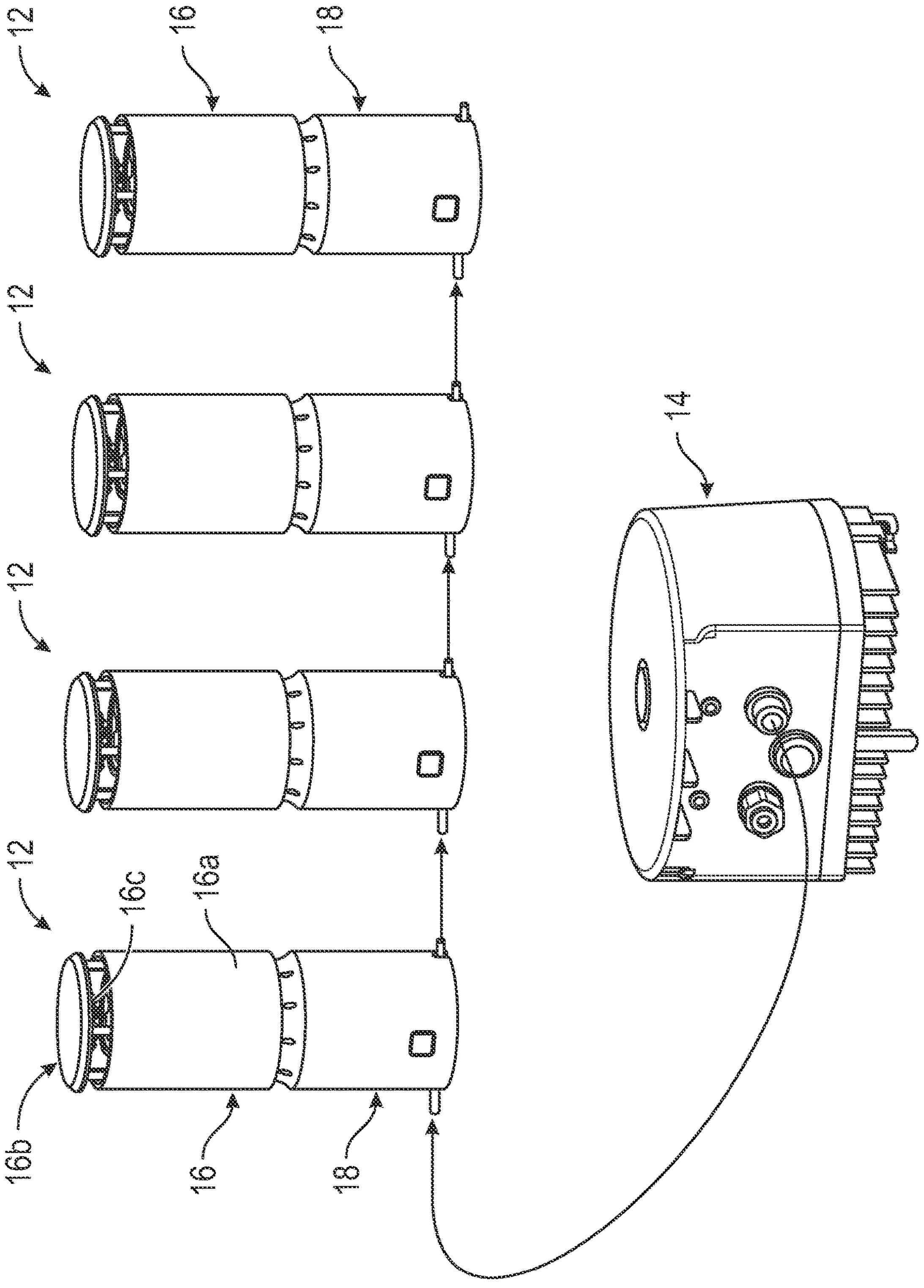
FIG. 2 is a schematic, perspective view of an embodiment of the linked insect repeller system of FIG. 1

Referring now to the drawings, there is illustrated in FIGS. 1 and 2 an embodiment of a linked insect repeller system, shown generally at 10. The linked insect repeller system 10 is illustrated having at least one repeller station (or emitter) 12 and a hub controller 14, though in other embodiments, the hub controller 14 may be integrated into the repeller station 12. The illustrated system 10 shows a plurality of stations 12 linked or daisy-chained together in series to form an area protected from insect intrusion. The stations may be connected in series, in parallel, or combinations thereof. As shown in the illustrated embodiment, the stations 12 are connected together and to the hub controller 14 to provide power and, in certain embodiments, control communications. The hub controller 14 may be connected to an electrical power source, such as a fixed base electrical source found in buildings and homes (typically 110/120 volts in the U.S. for example) or an environmental-generated power source such as a solar panel or wind turbine, or have a battery power source. The hub controller may include a step-down transformer or other means to provide a lower voltage output to the stations 12 when the input power is above the station power requirement. The hub controller 14 may further include an alternating current (AC) to direct current (DC) converter to provide a DC output from an AC input. In one embodiment, the hub controller 14 is connected to a higher voltage power source in the range of 110 to 120 volts AC and produces one of a 12 volt, 24, volt, 36 volt, or 48 volt DC output to power each of the repeller stations 12. Any desired input and output voltage combination is within the scope of the invention. In certain embodiments, the repeller system 10 may be battery powered by the individual repeller stations 12. In yet other arrangements, the repeller stations 12, either singularly or as a connected group, may be coupled to solar cell power elements. The hub controller 14 may send one or more control signals to each of the stations 12 to control each station's emission of insect repellent material, as will be described below in detail. The hub controller 14 and/or the repeller stations 12 may be connected through wired and/or wireless means.

The repeller station 12 includes an upper section 16 and a lower section 18. In the illustrated embodiment, the upper section 16 includes a shroud 16*a*, a cap 16*b* with a recycling shield 16*c*, and housing a heater assembly, shown generally at 20. A fluid reservoir 22 containing insect repellent material, and a wick 24 immersed in the fluid and extending out from the reservoir bottle are attached to the heater assembly 20. The shroud 16*a* provides protection to the interior elements, such as the heater and fluid container, and establishes a chimney effect in conjunction with the cap 16*b* and the lower section 18 to establish a convective air flow proximate to the wick or other vapor emitting structure. In the illustrated embodiment, the shroud 16*a* connects to the lower section 18 by cooperating bayonet and lug projections, though other closure mechanisms such as threads, pin and detent, snap fit mating structures may be provided. The shroud 16*a* may be made from any suitable material, though material selection and component design are made in conjunction with thermal energy transfer considerations.

Figure 3A:
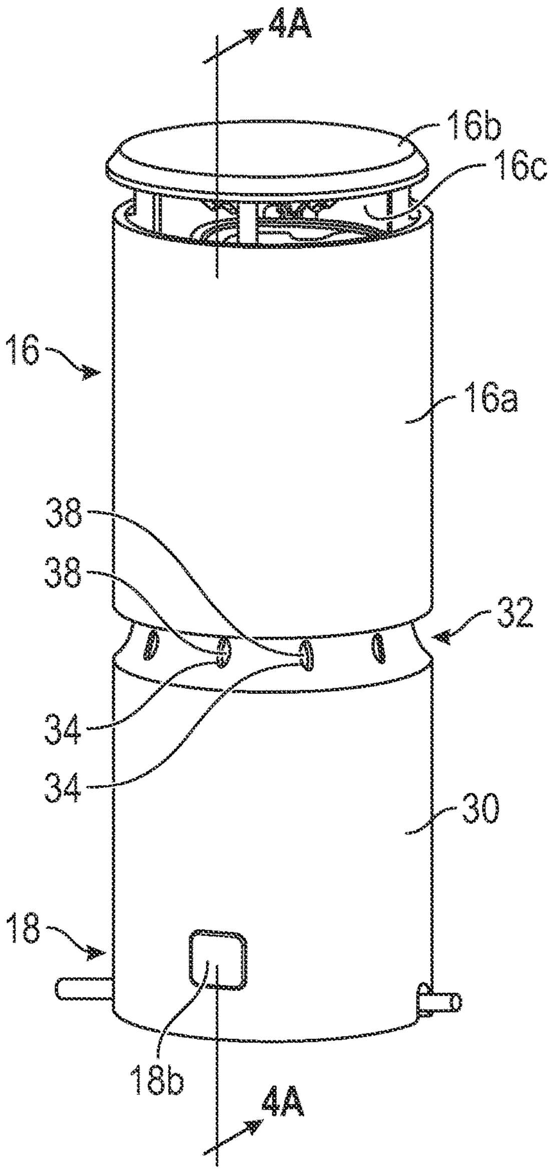
FIG. 3A is a front side, perspective view of an insect repeller station linked to the system of FIG. 2.
Figure 3B:
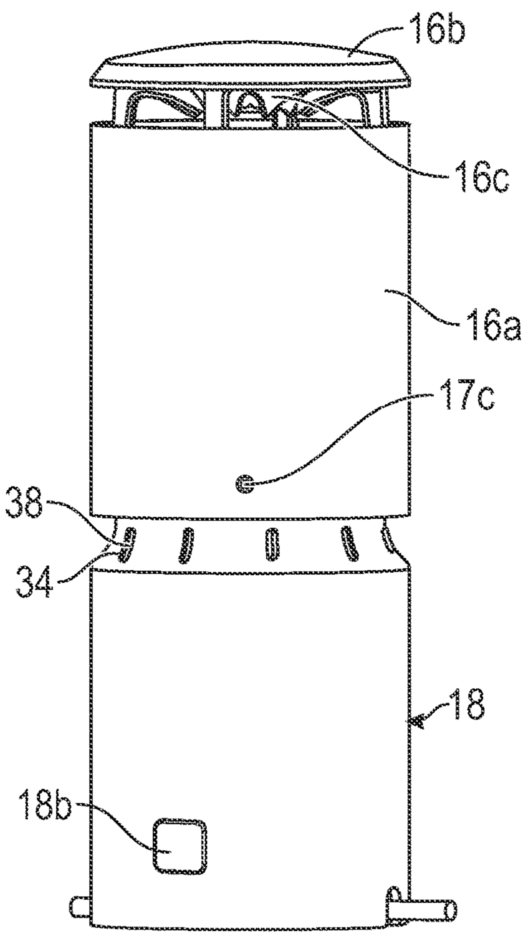
FIG. 3B is a rear side, perspective view of the insect repeller station of FIG. 3A.
Figure 4A:
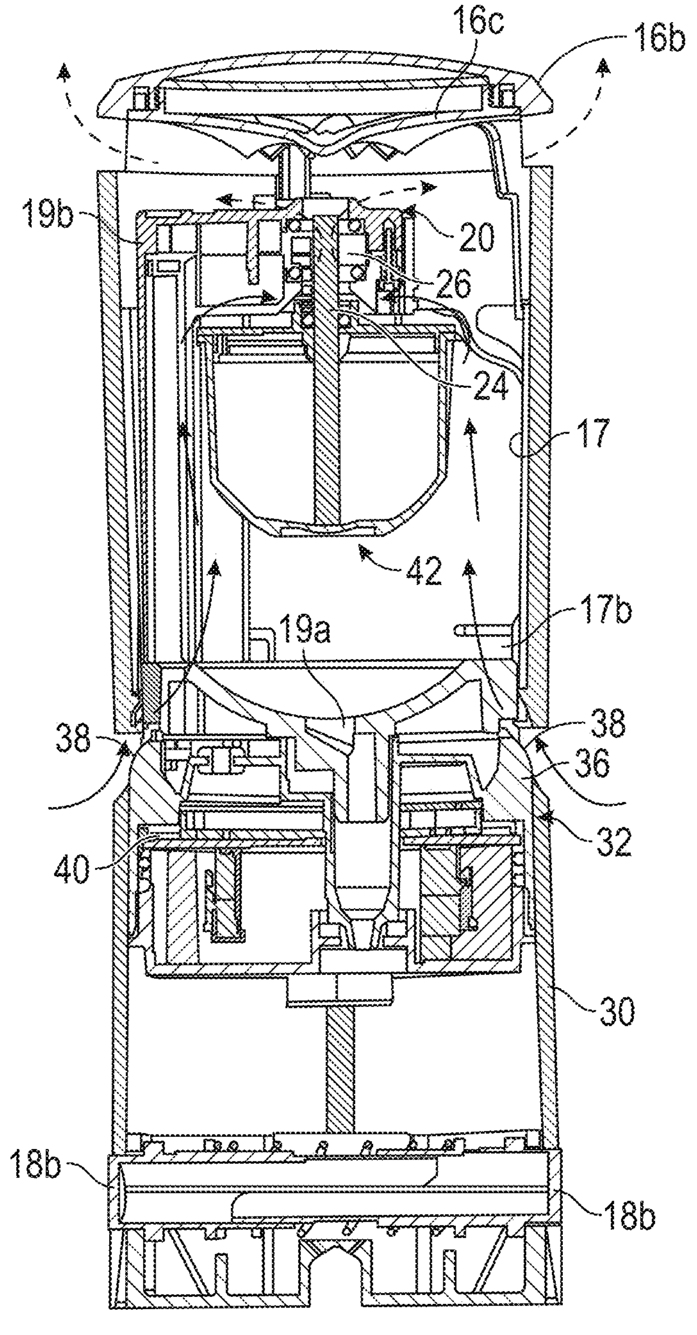
FIG. 4A is a cross section, elevation view of an embodiment of the insect repeller of FIG. 3A showing natural convective flow patterns.

In one embodiment, the shroud 16*a* may be made from a plastic or polymer material (ex. 20% glass filled polyphenylene ether—PPE based material, glass filed polypropylene, glass filled nylon, non-glass filled polymers) that insulates the interior volume of the shroud from environmental thermal loads, such as sunlight or surrounding thermal loads (dryer vents, structure thermal radiation, etc.), and thermal sinks, such as wind, water, shade, etc., and slows heat release from the interior volume that is generated by the heating element. In certain embodiments, it may be desirable to construct the shroud 16*a* from a metallic material, particularly for security and durability. As shown in FIG. 4A, an insulating jacket 17 is disposed inside (on, against, or spaced apart from the inner wall) the shroud 16*a*, though it may be disposed on, against or outside of the outer surface of the shroud 16*a*. In the illustrated embodiment, the insulating jacket 17 is configured with the circumferentially space bayonets 17*b* that engage corresponding lugs 17*a* on the lower section to retain the shroud. The bayonets 17*b* are configured as cantilever springs to deflect around the lugs and hook the shroud in place to the lower section 18. As shown in FIG. 3B, the upper housing further includes a locking feature, illustrated as a locking screw 17*c* that engages both the upper and lower sections 16 and 18 to prevent or impede inadvertent or unauthorized access to the interior area of the repeller station.

In general, material selection involves consideration of heat transfer between the structure and the vaporized repellent material. Structures that are subject to vapor contact may be chosen from materials that have relatively high specific heat, and thereby insulating properties. When these materials do not provide adequate structural or design performance, limiting the thermal mass of relatively low specific heat materials provides a quicker temperature equilibrium with the heated vapor material to minimize condensate formation. Where possible, limiting vapor contact with low specific heat materials also limits condensate formation. Since undesirable contact can draw heat away from the vaporized repellent, two negative effects tend to drive design considerations of the repeller structure and air flow routing:

Drawing heat from the vapor onto an adjacent surface trades kinetic energy in the vapor (that is working to move the vapor out of the repeller station), for potential energy in the station material that is waste (it warms the material surface).

If warm vapor cools on a surface, there is increased likelihood that the vapor will condense on that surface and not be exhausted from the repeller station, thereby not contributing to protected zone efficacy. Warming the surfaces reduces the potential for condensate formation, albeit at the cost of increased energy inputs.

Alternatively, actively or passively heating the repeller station materials may also be used as to reduce the two negative effects described above.

Figure 4B:
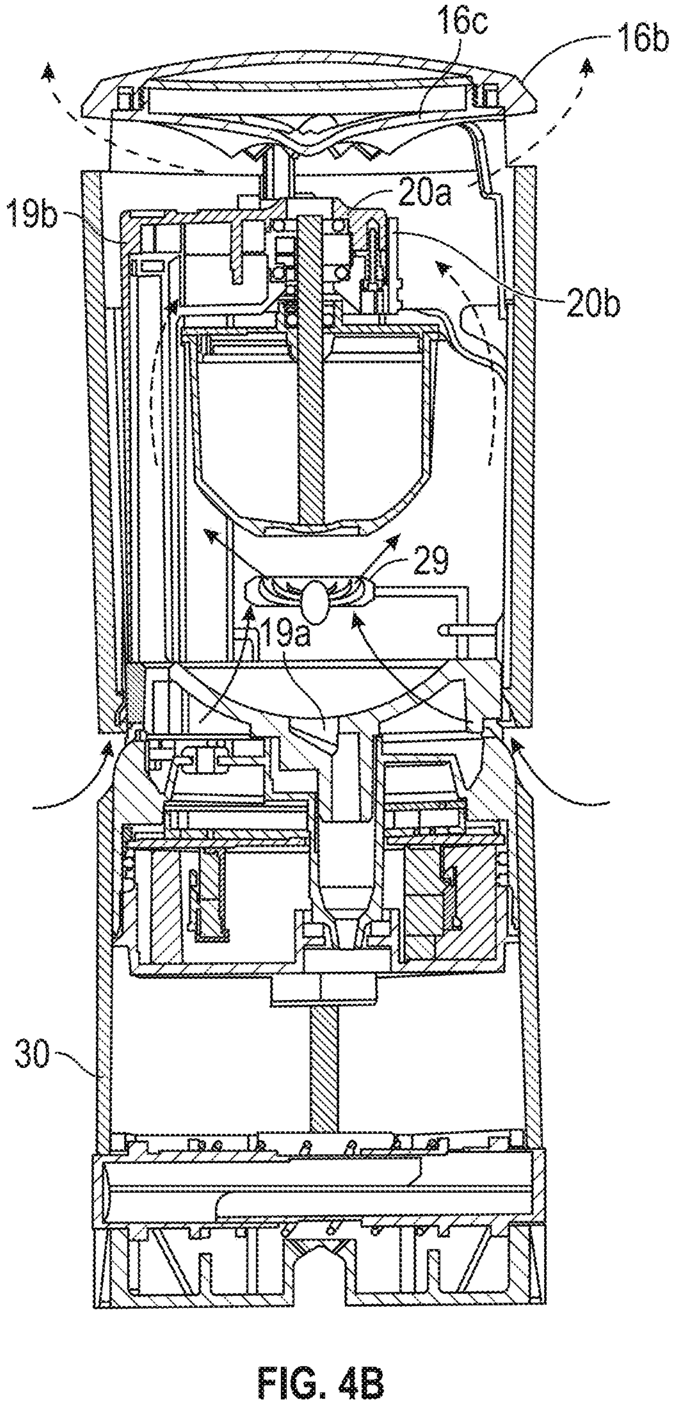
FIG. 4B is a cross section, elevation view of an alternative embodiment of the insect repeller of FIG. 3A having a forced convection mechanism.
Figure 4C:
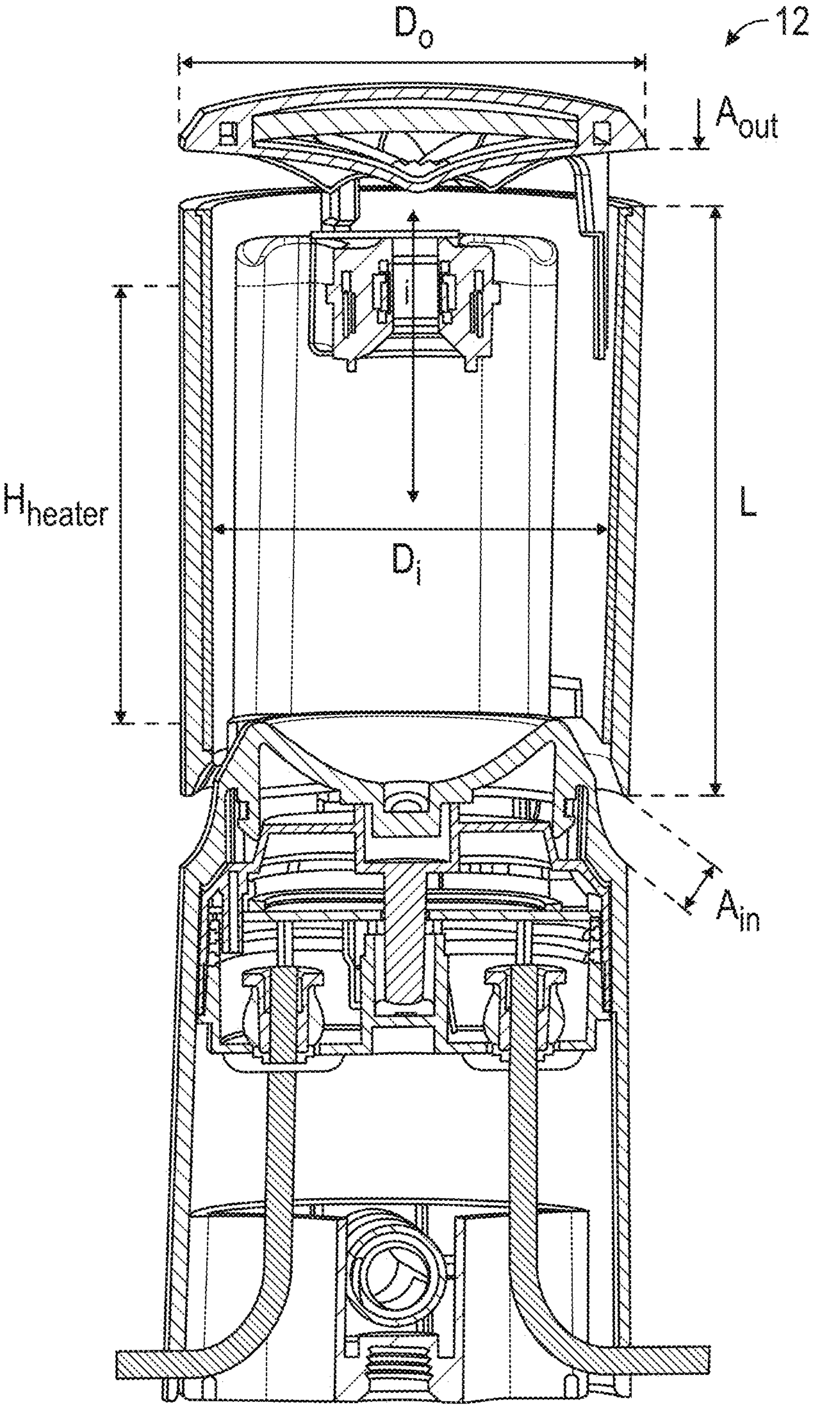
FIG. 4C is a cross section, elevation view of the insect repeller of FIG. 4A showing the dimensional relationship of the repeller structure impacting volatile emission performance.
Figure 4D:
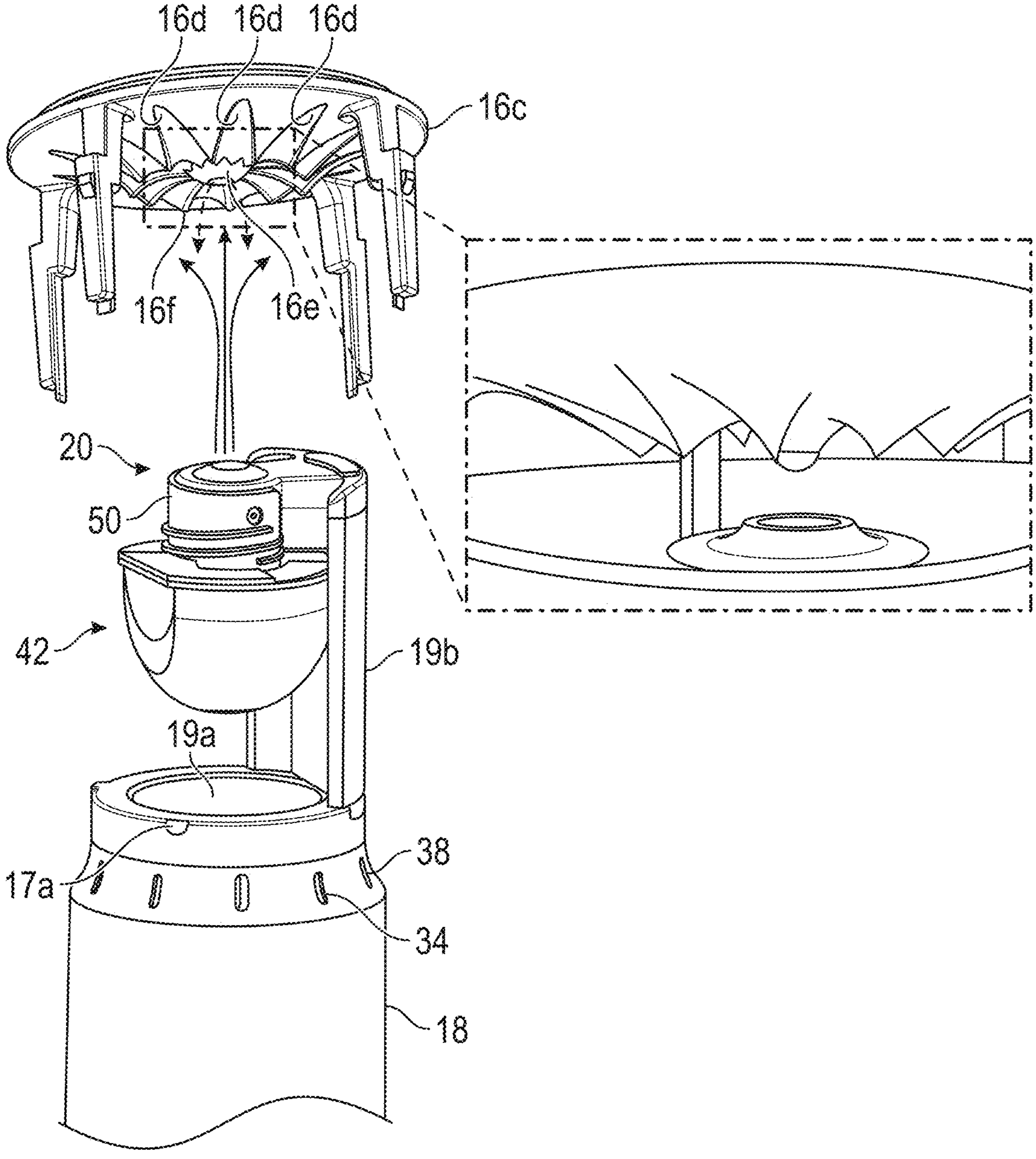
FIG. 4D is an exploded, perspective view of a recycling shield and heating assembly of the insect repeller of FIG. 4A.
Figure 5A:
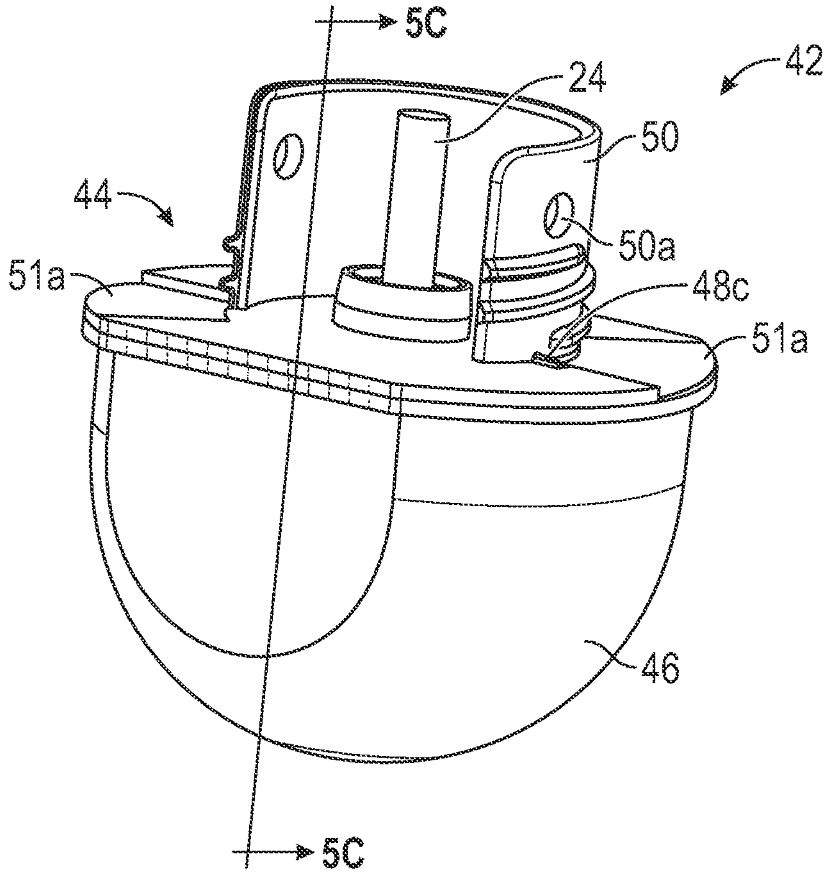
FIGS. 5A and 5B are perspective views of an evaporative fluid bottle having a reservoir, mounting hood, and wick (5A) and a cap (5B).
Figure 5B:
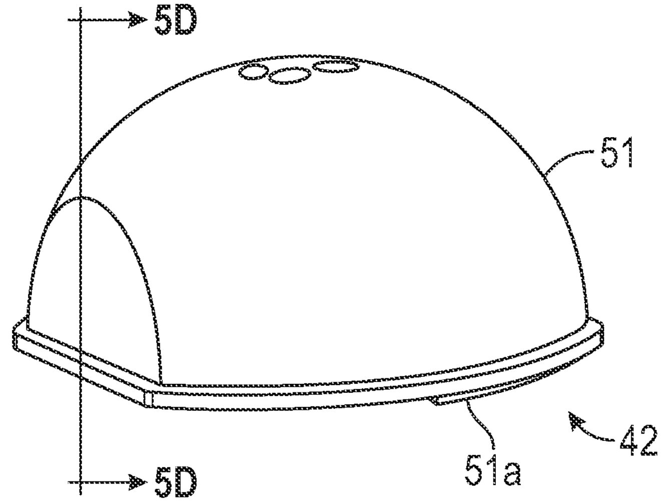
Figure 5C:
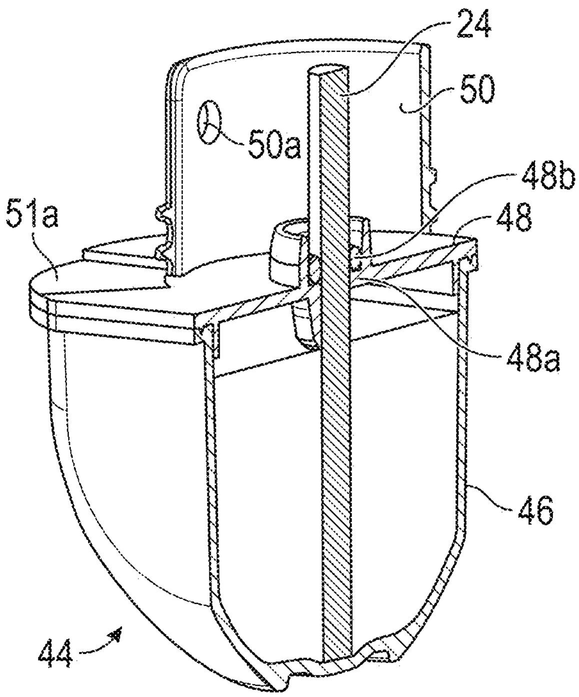
FIGS. 5C and 5D are perspective views, shown in cross section of the evaporative bottle and cap of FIGS. 5A and 5B.
Figure 5D:
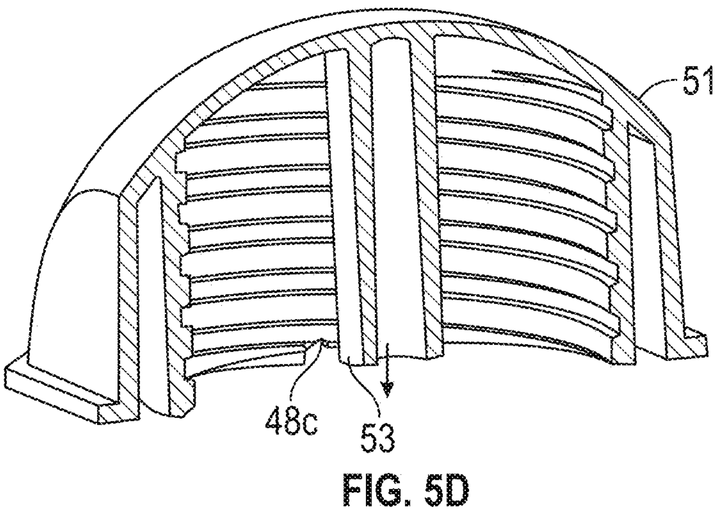

In one embodiment, the cap 16*b* is made of aluminum to provide durability and security, particularly in commercial or public access settings. The recycling shield 16*c* may be made of an insulating material to shield vapor exposure to large temperature differentials. In other embodiments, the recycling shield 16*c* may also be made from a low specific heat material, such as aluminum, titanium, steel, or other metals, and include a structure to ameliorate the formation of any condensate. As shown in FIGS. 4A-4C, the recycling shield 16*c* is shown in cross section and is configured as a thin walled structure that reduces material mass to minimize heat absorption. Since the recycling shield 16*c* is proximate to the heat source, the thin structure can absorb a lower amount of heat energy to achieve thermal equilibrium with the interior volume. When a large temperature differential exists sufficient to cause condensate formation on the cap 16*b* and recycling shield 16*c*, a condensate collection and redirection structure may be provided to guide condensed vapor back to the wick for reuse. As shown in FIG. 4D, the condensate collection and redirection structure of the recycling shield 16*c* includes a plurality of troughs 16*d* that facilitate air and vaporized repellent material to flow from the wick and surrounding area out of the station. The illustrated troughs have a fluted shape that permits air flow outwardly and directs any condensate material back toward the heater assembly. As further shown in FIG. 4D, the condensed droplets collect at a condensate accumulation point, illustrated as a center boss 16*e* having a general hemispherical shape or an acorn-like shape terminating in a pointed end, positioned above the wick to guide droplets to fall onto the wick. Adjacent troughs 16*d* define partitions that help deflect external sources of water or liquid contamination away from the heater. As shown in FIG. 4C, the outer array of partitions form guides 16*f* that direct intruding water away from the wick. The guides 16*f* have a cathedral shape forming peaks or points arranged in a diameter outside of the heater. A consideration in the structure of the guides is to not impede the convective flow of vaporized material from the repeller station. The guides 16*f* collect intruding water that forms into droplets and collect at the point and fall outside of the wick toward the lower section 18. As shown in FIGS. 4A-4C, a collection bowl and drain 19*a* permits water blocked and directed by the guides 16*f* to be gathered and ducted out of the station.

As shown in FIGS. 4A-4D, the recycling shield 16*c* is positioned under the cap 16*b* and may be either a separate component or integrally formed with the cap. Alternatively, the cap, recycling shield and upper shroud may be formed as a single unit. The cap 16*b* attaches to the shroud 16*a* and forms an outlet vent or series of outlet vents between the shroud and the recycling shield to exhaust vaporized insect repellent material. Alternatively, the outlet vent may be a series of openings. The size and spacing of these openings impact vapor flow and station efficiency, as will be described below.

The wick 24 extends into a heater or heating element 26 of the heater assembly 20, illustrated as encircling the wick. The heating element may be a single heating element or a series of segmented heating elements positioned at various points around the wick perimeter. The heating element vaporizes the repellent material taken up by the wick through capillary action. The shroud 16*a* defines an air inlet 28*a*, between the lower section 18 and the end of the shroud proximate to the lower section, and an air/vapor outlet 28*b* between the cap 16*b* and the shroud end proximate to the cap. As shown in FIG. 4A, the air inlet 28*a*, in conjunction with the heater assembly 20, establishes a natural convective current that disperses the vaporized repellent material. As shown in FIG. 4B, a fan 29 or other structure may provide a forced convection flow of air to spread the vaporized repellent material.

As shown in FIGS. 4A-4C, the heating assembly 20 is mounted on a support arm 19*b* and cantilevered to the center of the interior volume of the shroud 16*a*. In the illustrated embodiment, the heating assembly 20 is positioned toward the upper portion of the upper section to promote a chimney effect in the volume of the upper section to establish a natural convective flow pattern. As shown in FIG. 4C, the heater assembly is positioned at a height, $H_{heater}$ above the lower section 18. The support arm 19*b* includes a conduit passage to permit electrical connections between the controller and the heater 26. The support arm 19*b* connects to or is integrally formed with one of an upper heater housing 20*a* or a lower heater housing 20*b*. As will be explained below, the support arm 19*b* and/or the heater housings 20*a*, 20*b* may include fluid level sensing structures to determine actual fluid levels of active ingredient as the device is used. Alternatively, the fluid level may be calculated based on run time of the units, the known starting levels, and known volatilization rates based on heater operation and wick construction.

Referring to FIG. 4C, the interfaces of the lower section 18 and the shroud 16*a* along with the shroud 16*a* and the cap 16*b* defines the inlet and outlet openings that establish air flow parameters, such as velocity and volume flow through the station to gather and disperse the volatized materials into the surrounding area to establish a pest control area. The interfaces form a mechanical fixture design that, combined with the heat generated from the heater, enables a velocity profile to distribute the vaporized repellent out of the station sufficient to produce the pest control area. In one embodiment, the velocity and volume output of volatilizable insect repellent material establishes a pest control zone of approximately the 20 feet in diameter around the unit (measured without wind effect). The velocity of air flow through the unit in conjunction with the heat from the heating assembly utilizes the chimney effect of the upper section to create a natural convective flow therethrough.

As shown by the solid and dashed arrows, an air velocity profile travels from the lower air inlet section 28*a* of the station, through the shroud 16*a*, around the wick, and upwards and outwards through the outlet 28*b*. The air inlet 28*a* and air/vapor outlet 28*b* are configured with cross-sectional areas designed with consideration of the temperature gradient between the heat source forming the vapor and the ambient temperature. In one embodiment, the selected temperature gradient is defined as a 103° C. ΔT at the heater from a 20° C. ambient temperature. A resulting air inlet cross-section, $A_{in}$, of approximately 340 $mm^2$, located about 113 mm below the heat source, creates upward airflow through the shroud 16*a*, exiting the air/vapor outlet, $A_{out}$, having a 2580 $mm^2$ area. The outlet (or outlets) is a generally, uniformly distributed air outlet cross-section located approximate 5-10 mm above the heat source. The shroud 16*a* may have an inner diameter $D_i$ of about 72 mm at the interface with the lower section 18, an inner diameter of about 77 mm at the junction of the outlet openings and an overall length L of about 108 mm. This tapered arrangement also assists in promoting the natural convective air flow and chimney effect through the unit through a venturi effect. The repeller may further have an outer diameter of about 87 mm at the interface with the cap 16*b*. These dimensions relate to a specific embodiment of the insect repeller system and may more broadly define a range of dimensions where the at least one inlet opening defines an air inlet cross-section of in a range of about 300-400 $mm^2$, the outlet opening defines an air/volatilizable insect repellent material outlet cross section in a range of about 2450-2650 $mm^2$, and the separation distance in a range of about 95-115 mm. The heating element may be in a range of about 100-120 mm above the inlet opening.

In the illustrated embodiment, the inlet 28*a* and outlet 28*b* are of fixed cross sectional areas. Alternatively, the inlet and outlet openings may be varied, either manually or automatically by rotatable louvers that move between open and closed positions. In determining the size and layout of the shroud 16*a* and openings 28*a* and 28*b*, certain design considerations help define the overall emission performance of the repeller station. The design parameters of inlet area, outlet area, temperature gradient, shroud diameter, and shroud length (defining separation distance between inlet and outlet) can be varied to affect air velocity through the unit which affects vapor output and repellent zone performance. Referring to FIG. 4C, with other design parameters fixed, varying single parameters of the mechanical configuration has been found to produce the following effects on unit performance:

- Increased outlet air cross-section, $A_{out}$, does not (or minimally) boost air velocity through the emitter.
- Increased inlet air cross-section, $A_{in}$, does not (or minimally) boost air velocity through the emitter.
- Reduced inlet air cross-section, $A_{in}$, restricts air velocity through the emitter.
- Reduced outlet air cross-section, $A_{out}$, restricts air velocity through the emitter.
- Reduced temperature gradient restricts air velocity through the emitter.
- Increased temperature gradient boosts air velocity through the emitter.
- Increased distance, L, between inlet and outlet boosts air velocity through the emitter before effects of drag/friction and system losses are accounted for.
- Reduced distance, L, between inlet and outlet reduces air velocity through the emitter before effects of drag/friction and system losses are accounted for.
- Increased body diameter, average of $D_o$ and $D_i$, can reduce system losses and flow restrictions enabling increased air velocity through the emitter until system losses become negligible.
- Reduced body diameter, average of $D_o$ and $D_i$, can increase system losses and flow restrictions reducing air velocity through the emitter.

To facilitate air flow through the station and improve zone development and active ingredient concentration in the surrounding zone, reducing turbulence has a positive impact on system performance. The exit surfaces are formed to be generally smooth with rounded or curved features to minimize turbulence in the air/vapor stream and reduce system losses. The surfaces may be polished or coated to help achieve a smooth finish.

In addition to air flow, the concentration of active ingredient in the volatized fluid, the wick material, and the heating temperature impact repellent zone formation. The wick 24 extends into the fluid and draws material by capillary action. The capability action of the wick 24 to provide a high-flow draw of material relates to the wick material porosity. Extruded fiber wick compositions or sintered plastic materials provide adequate flow characteristics for an active ingredient concentration of about 4.5-6.5% metofluthrin and a heater temperature range of about 60-70° C. In a preferred embodiment, the concentration is about 5.5% metofluthrin. The wick flow characteristic forms the input design parameter to determine the necessary air velocity to establish a desirable and effective insect-free zone. In one aspect of the invention, an emission rate of about 200 mg/hr of 5.5% metofluthrin facilitates forming a 20 foot diameter zone using the above referenced structural dimensions.

In the illustrated embodiment, the lower section 18 includes a housing shell 30 that supports a light assembly, shown generally at 32, and has at least one light port 34. In the illustrated embodiment, the at least one light port is a plurality of light ports though other illumination arrangements may be provided. The light assembly 32 preferably includes light emitting diode (LED) light sources, though any light emitting means may be used. The light assembly 32 includes a light pipe 36 having light emission points 38 that align with the light ports 34 to generate a visible light pattern. Behind the light pipe 36 is an LED lighting assembly comprising at least one light emitting diode (LED) 40, a plurality of LEDs are shown. The LEDs are selectively powered by hub controller and may be used to indicate an operational status, for decorative purposes, or both. In one embodiment, the operational status of the unit may be indicated by both light color and flashing or strobe effects. For example, as the unit is started and the heating element warming, an amber colored "chasing" LED effect may be broadcast to indicate a start mode condition. When the station achieves operating temperature, a continuous blue or other user-defined color may be shown. Examples of lighting sequences indication operational status is shown in the table below:

| LED Sequence | Description |
|---|---|
| Amber Chasing LED | Unit is warming up Protection Zone is not ready |
| Solid Thermacell Blue/ User Selected Color | Unit is at temperature and the Protection Zone is ready |
| Periodic Red LED Flash | Unit Cartridge is getting Low<br>10 minutes between Red Flash <– Cartridge at 25%<br>5 minutes between Red Flash <– Cartridge at 10%<br>30 Seconds between Red Flash <– Cartridge at 5% |
| Solid Red LED | Unit Cartridge is empty |
| RED/BLUE Flash | Unit is in an Oven Temp Fault State |
| RED/WHITE Flash | Unit is in a Blown Fuse Fault State |
| RED/AMBER Flash | Unit is in a Warming Timeout Fault State |
| Hub WiFi LED-Slow Blink | WiFi not Connected to Network |
| Hub WiFi LED-Solid | WiFi Connected to Network |
| Hub WiFi LED-Rapid Blink | Error Detected |
| Hub Power LED-Off | DC Voltage not Present on Hub PCBA (3.3 V DC) |
| Hub Power LED-Solid | DC Voltage Present on Hub PCBA (3.3 V DC) |
| Halo LEDs-Solid | Repellers Enabled |
| Halo LEDS-Off | Repellers Disabled |
| Halo LEDs-3x Blink | Button Press Refill Life Clear Selected |
| Halo LEDS-Rapid Blink | Button Press Factory Reset Selected |

The lower section 18 includes a fixed base mounting interface 18*a* that permits attachment of various mounting structures to provide an array of positioning choices when installing the linked insect repeller system. A retaining mechanism, illustrated as a spring loaded pair of opposing snap-fit buttons 18*b*, extend through detents or apertures formed in the lower housing 18 and the mounting interface 18*a* to secure the components together. The mounting interface 18*a* includes an attachment point 18*c*, illustrated as a threaded bore in FIGS. 4A-4C, that accepts a complementary attachment of mounting structures, such as those of FIGS. 9A-9D as will be described below.

Referring to FIGS. 4A-4C, 5A-5D, and 6A-6B, an embodiment of an evaporator bottle, shown generally at 42, is illustrated in conjunction with the repeller station. The evaporator bottle includes a refill bottle 44 having a fluid reservoir 46 and a reservoir cap 48. The fluid reservoir 46 is illustrated having a general bowl shape with opposing flat faces, though any reservoir geometry such as spherical, cylindrical, oblong spherical, square, rectangular, triangular, or any multi-faceted or smooth geometry may be used and is contemplated by the invention. The reservoir cap 48 includes a wick port 48*a* and at least one seal 48*b* that contacts the wick 24 to prevent fluid leakage from the reservoir. The seal is illustrated as an O-ring, though other sealing geometries, such as a flat washer seal, may be used. The wick 24 has a clearance fit with the wick port 48*a* to permit admission of air into the reservoir 46 for venting purposes. The reservoir cap 48 includes a reservoir neck or mounting hood 50 that has an outer attachment structure to interface with a bottle lid 51 for maintaining the integrity of the wick 24 and the fluid contents of the reservoir 46 during handling and shipping. In the illustrated embodiment, the outer attachment structure is shown as threads; however, other attachment means such as snaps, barbs, interference fits, and the like may be used to retain the bottle cap onto the evaporator bottle. In an alternative embodiment, the mounting hood 50 may be two or more mounting legs as shown. In yet another embodiment, the reservoir cap may eliminate the mounting hood and include a magnet or metal target (such as a washer encircling the wick port) and the heater assembly may carry the other of the magnet or target as an alternative mounting configuration.

The bottle lid 51 and the reservoir cap 48 include an anti-overtightening interface comprising mating ramps 51*a* and detents 48*c* that interact to secure the lid in a closed position and provide a stop to prevent overtightening. In addition, the interface creates an alignment of the geometric features of the bottle lid with the reservoir to provide an aesthetically appealing assembly and align flat areas to facilitate the twisting motion to open the refill. The mating ramps are sloped to create a latch/lock interface that further prevents inadvertent loosening and backing out of the cap from the bottle.

The mounting hood 50 encircles a portion of the wick, illustrated as approximately 60% though completely encircling the wick may be used in conjunction with a complementary mounting interface of the heater assembly. As shown in FIGS. 4A-6B, the mounting hood 50 has an open section that accepts a mating mounting interface 52 on the upper and/or lower heater housings 20*a* and 20*b* of the heater assembly. In the illustrated embodiment, the upper heater housing 20*a* includes at least one bottle support structure, illustrated as an attachment boss 54, that permits the mounting hood to be retained to the heater assembly. Alternatively, the upper or lower heater housing or a singularly formed heater housing may secure the bottle to the station. In the illustrated embodiment, mating detents 50*a* in the hood 50 engage the attachment bosses 54 in a snap-fit engagement. Alternatively, the bosses 54 may be formed on the hood 50 and extend into detents formed into the housings 20*a* and/or 20*b*. The mounting hood 50 also provides alignment of the wick to the center of the heating element. In one embodiment, the reservoir is configured to hold enough insect repellent material for prolonged operation, such as operation over an insect control season. For different parts of the country or different applications the insect control season may be in a range of 1-2 months, 3-4 months, or 6 months. Alternatively, the reservoir may contain any desired amount of fluid.

Figure 6A:
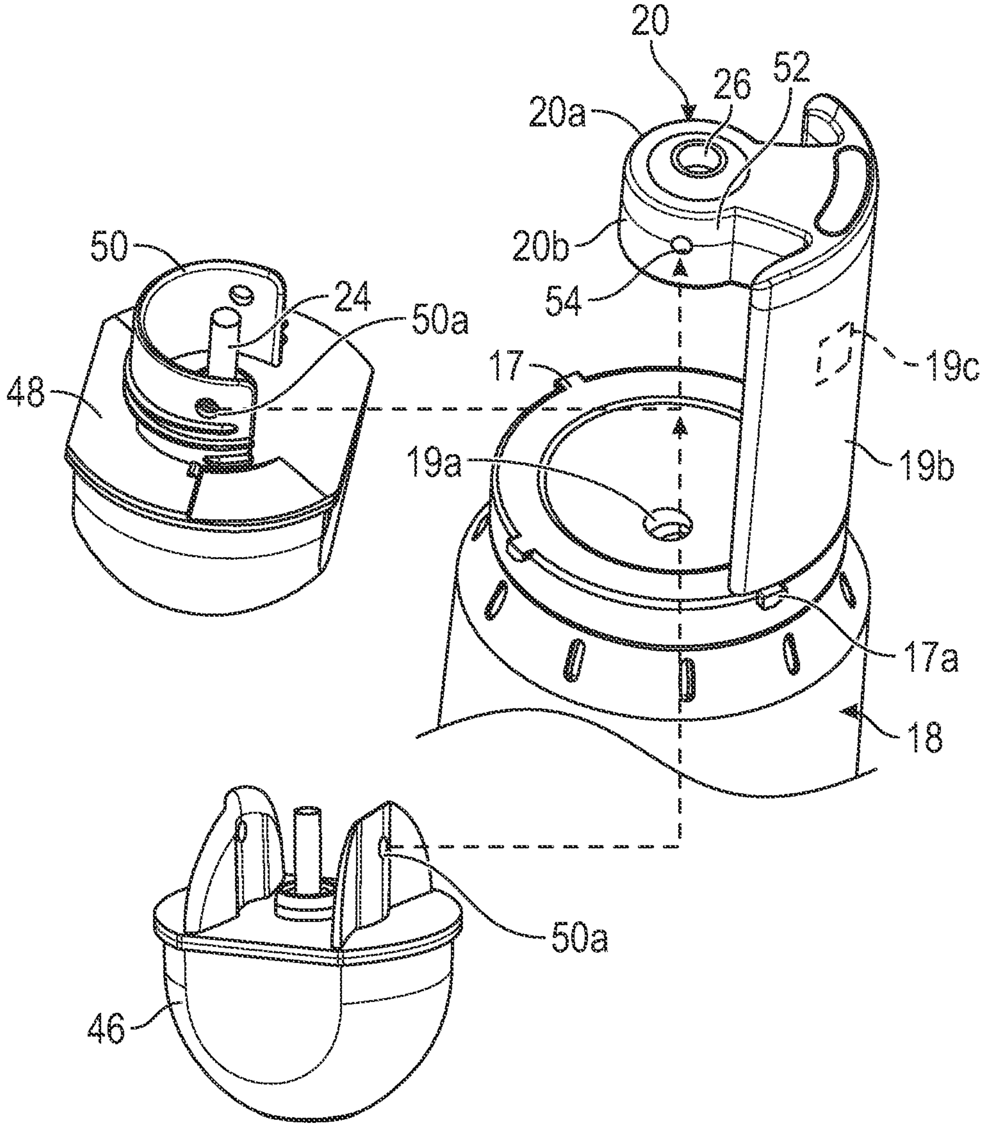
FIGS. 6A and 6B are perspective views of the evaporative fluid bottle of FIG. 5A and the connection to the heater assembly of the repeller station of FIG. 4A.
Figure 6B:
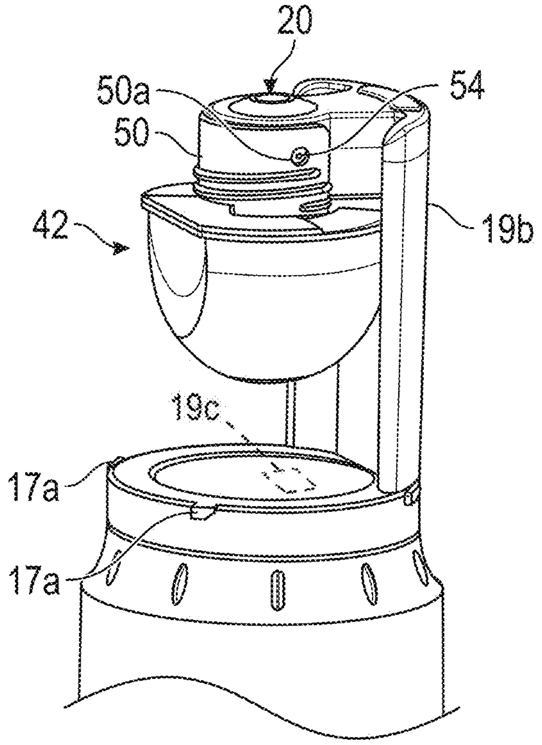
Figure 6C:
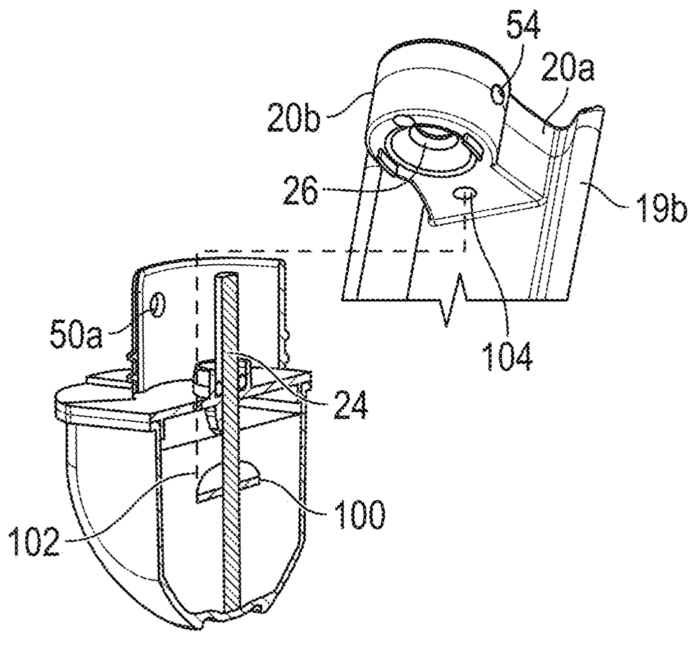
FIG. 6C is a cross-sectional view of an evaporator bottle having a fluid level indicator.

In certain embodiments, the amount of fluid contained in the reservoir 46 may be measured or determined by various means. In one embodiment, the repeller station 12 may include the ability to measure and monitor the weight of the evaporator bottle 42 and changing fluid level. In one aspect, the support arm 19*b* or upper or lower heater housings 20*a*, 20*b* may include a weight scale 19*c*, for example a strain gauge or load cell, shown schematically in FIG. 6A and FIG. 6B. Alternatively or in conjunction with the support arm or housings, the weight scale 19*c* may be connected to the attachment bosses 54 to detect weight changes in the bottle as fluid is withdrawn. In another aspect, the support arm 19*ab* or lower housing may include the weight scale 19*c* configured as an infrared (IR) sensor to optically measure the fluid level in the bottle. In certain embodiments, the evaporator bottle 42 may carry part or all of the fluid level detection device. In one embodiment, the bottle 42 may include a float 100 and plunger 102 that contacts a sensor or switch 104 in the lower housing 20*b*, as shown in FIG. 6C. When a full bottle is attached to the heater housing 26, the float 100 may be pushed down into the fluid by the plunger 102 contacting the switch or sensor 104 in the lower housing 20*b* to a "low level indicated" portion of the bottle that may represent 25% fluid remaining. As the switch is contacted, either in an open or closed state, the system considers the fluid level to be in an acceptable range and does not signal a low fluid condition. As the fluid is withdrawn, the buoyancy of the float permits it to rise to the surface of the fluid. When the fluid level is reduced to a level where the buoyancy of the float reaches equilibrium with the surrounding fluid and it floats on the fluid surface, additional fluid loss causes the plunger to lose contact with the switch and the threshold low level is detected. In this embodiment, the float and plunger may act as a plug and the aperture through which the plunger extends acts as a vent. Thus, the float seals the vent and the plunger opens the vent when the bottle is installed.

Figure 7A:
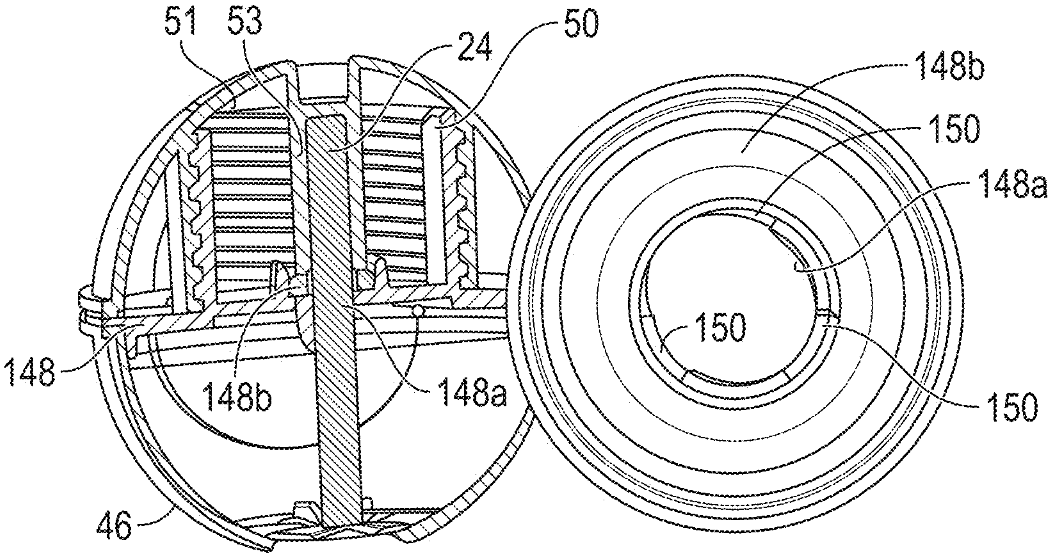
FIG. 7A is a cross-sectional view of an embodiment of a bottle venting structure.
Figure 7B:
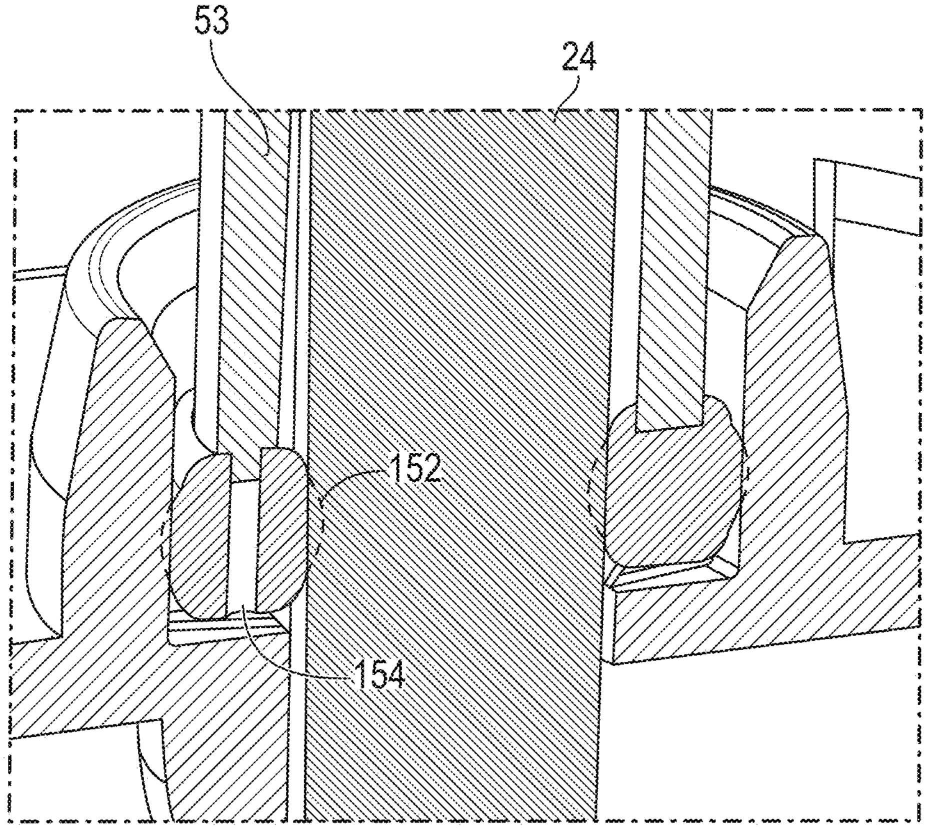
FIG. 7B is a cross-sectional view of a seal-based bottle venting structure.
Figure 7C:
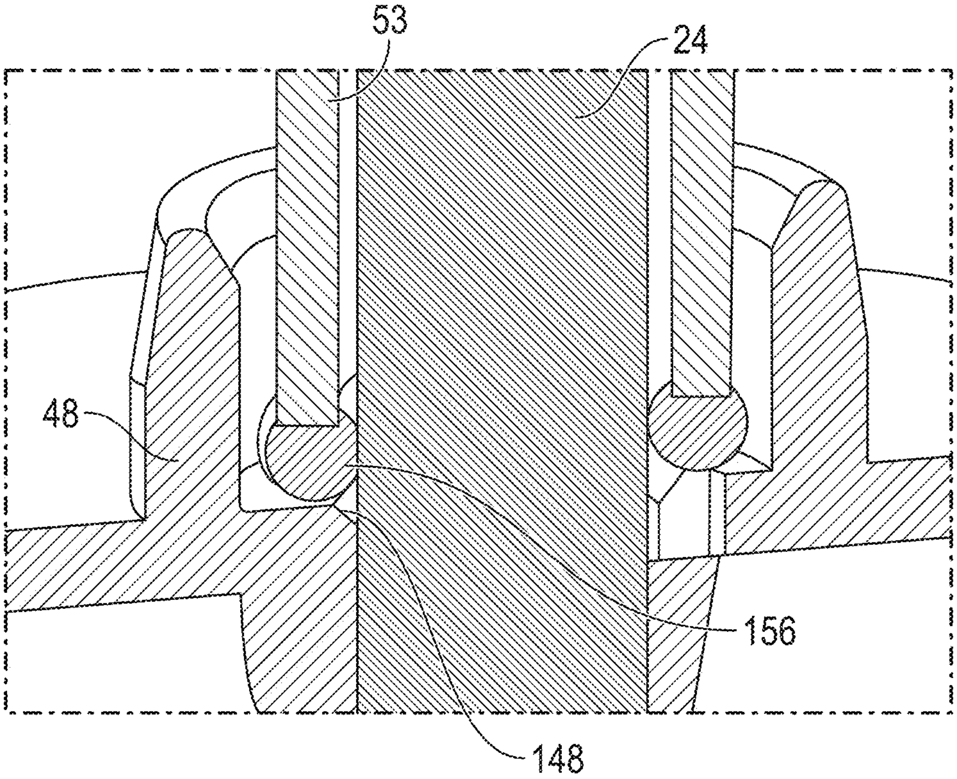
FIG. 7C is a cross-sectional view of a cooperating wick and seal bottle venting structure.
Figure 7D:
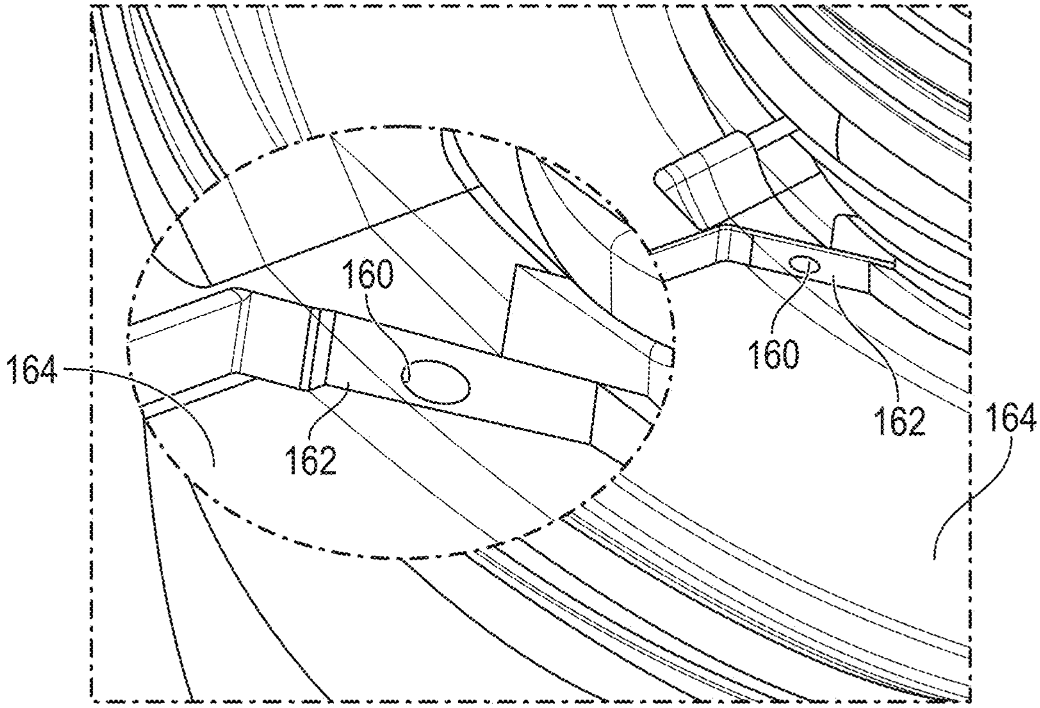
FIG. 7D is a cross sectional view of another embodiment of a bottle venting structure.

Bottle venting is one consideration to facilitate capillary action of the wick and prevent fluid loss during shipping and handling. If the reservoir bottle is not adequately vented, as fluid is drawn up by the wick a vacuum forms in the bottle preventing adequate draw of material. Referring now to FIGS. 7A-7B, variations of reservoir bottle venting structures are illustrated. These bottle venting structures cooperate with portions of the reservoir cap to close off the fluid vent embodiments. As shown in FIG. 7A, the wick extends through a wick port 148*a*, similar to wick port 48*a*, of a bottle cap 148. The wick port includes at least one slot 150, three are illustrated, that extends along the wick 24 and in fluid communication with the fluid reservoir 46. Air is permitted to pass between the wick 24 and the wick port 148*a* through the slots 150. A seal 148*b* encircles the wick 24. When the bottle lid 51 is attached to the hood 50 in a closed position, a wick protector 53 contacts the seal 148*b* and deflects the seal into contact with the wick and the cap 148 to close off the slot 150 to prevent fluid leakage from the reservoir. Referring now to FIG. 7B, an alternative seal 152, configured as an O-ring and having a vent port 154 formed therethrough and may be generally parallel to the wick. The wick protector 53 contacts the vent port 154 and closes the pathway to the reservoir to prevent fluid leakage. FIG. 7C illustrates another variation of a seal interface with the wick 24 where a seal 156 contacts the wick and has a loose or clearance fit with the cap 48. The wick protector 53 contacts the seal 156 and compresses it against the cap to close off the wick port, such as wick ports 48*a* or 148*a*. FIG. 7D illustrates an alternative vent 160 formed through an end wall of a ramp 162 of a bottle cap 164, similar to the detent 48*c* of cap 48. The ramp 51*a* of lid 51 seals off the vent 160 when in the closed position.

Figure 7E:
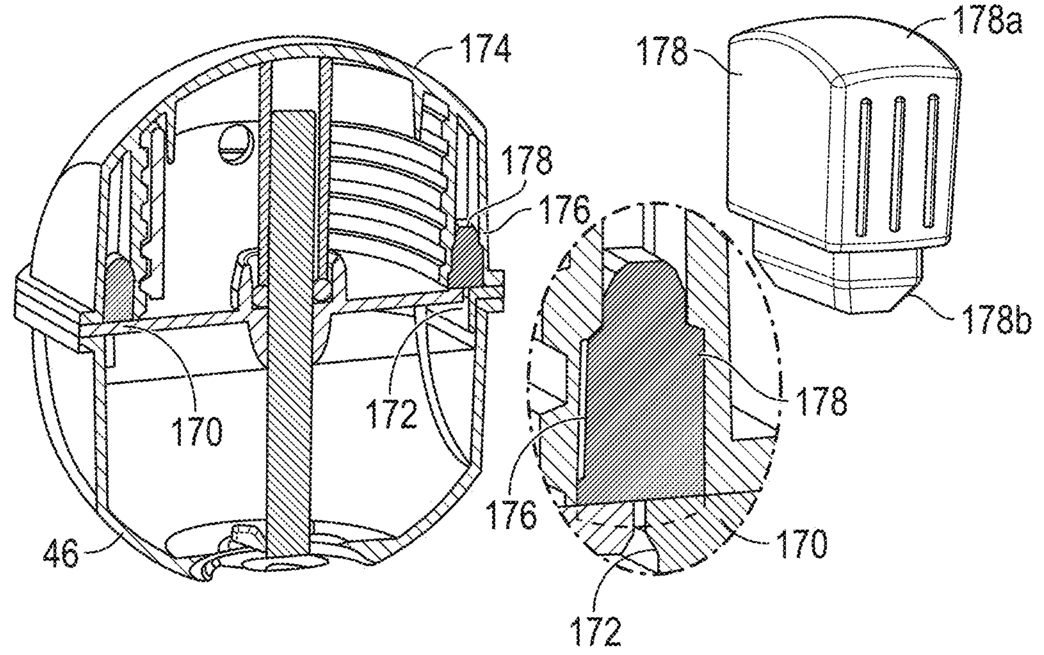
FIG. 7E is a cross-sectional, perspective view of another embodiment of a bottle venting structure.
Figure 7F:
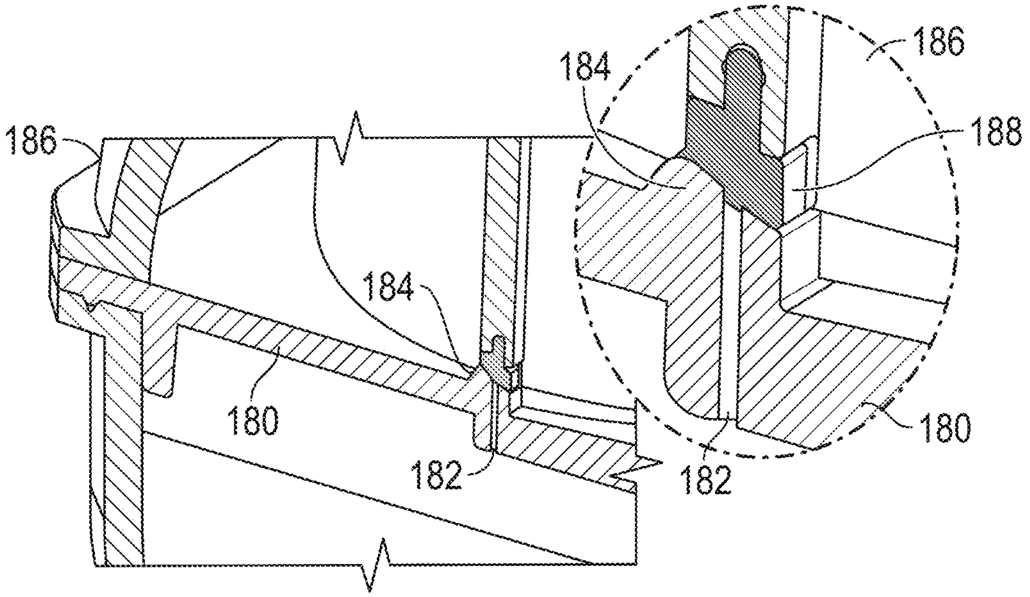
FIG. 7F is an enlarged, cross-sectional view of another embodiment of a bottle venting structure.

FIGS. 7E and 7F illustrate alternative vent sealing mechanisms that are carried by the cap. As shown in FIG. 7E, a bottle cap 170 closes the reservoir bottle 46, similar to those described previously, and includes a vent port 172. The vent port 172 is positioned near the outer edge of the cap 170. A lid 174 includes a seal housing 176. A seal 178, illustrated as rectangular though any geometric shape may be use, has a generally convex sealing surface 178*a* that contacts the surface of the cap 170 and covers the vent port 172 when the lid is secured to the hood. The seal 178 may also include a retaining end 178*b* that engages a corresponding structure in the seal housing 176 to retain the seal within the seal housing. In an alternative seal arrangement depicted in FIG. 7F, a cap 180 includes a vent 182 formed through a stop detent 184, similar to detent 48*c* described above. A lid 186 carries a seal 188 that contacts the stop detent 184 and closes off the vent 182 when the lid 186 is moved to the closed position.

Figure 8A:
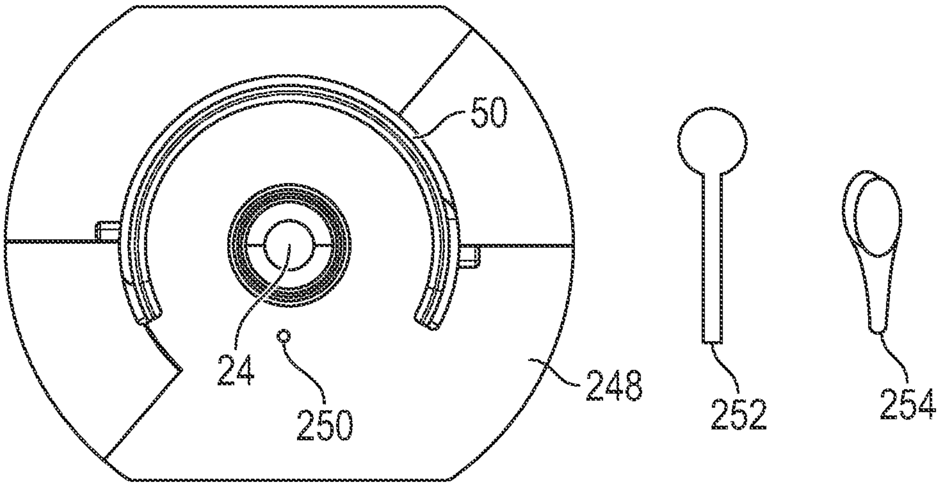
FIG. 8A is a top view of a bottle venting structure with alternative removable vent closures.
Figure 8B:
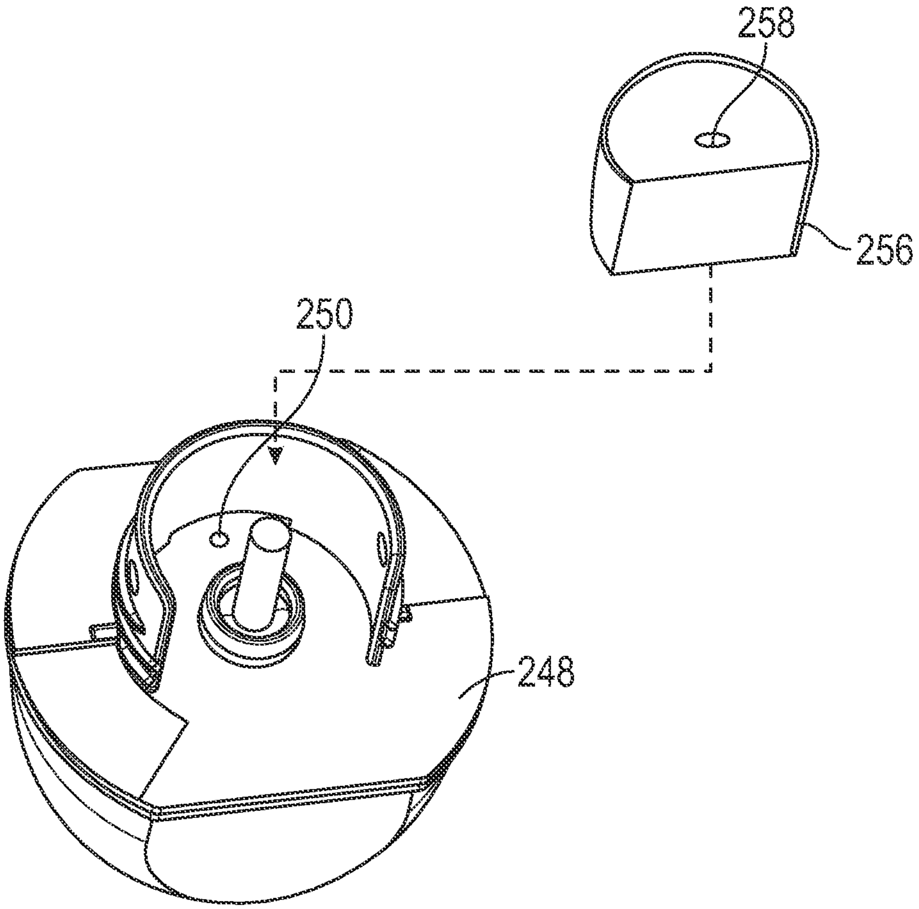
FIG. 8B is a perspective view of another embodiment of a removable vent closure.

As shown in FIGS. 8A and 8B, removable vent closures are illustrated that can be removed and discarded prior to installation of the reservoir bottle to the repeller station. A reservoir cap 248 includes a vent port 250, illustrated as an aperture, that is formed therethrough. In FIG. 8A the vent port 250 is positioned generally in the open portion of the hood 50 and may be closed off by a removable tab 252 that is adhesively attached to the cap 248 over the port. Alternatively, a plug 254 may be inserted into the port 250. As shown in FIG. 8B, a sealing block 256 with an aperture 258 closes off the vent port 250, now shown between the wick and hood. The aperture 258 accommodates the wick protector 53 and the lid compresses the block against the port.

Figure 9A:
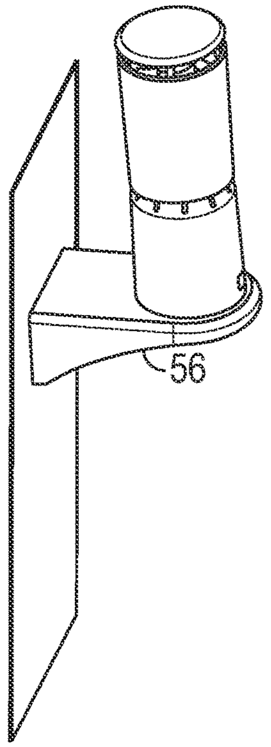
FIG. 9A is a perspective view of an embodiment of a vertical surface mounting bracket coupled to the insect repeller station of FIG. 3A.
Figure 9B:
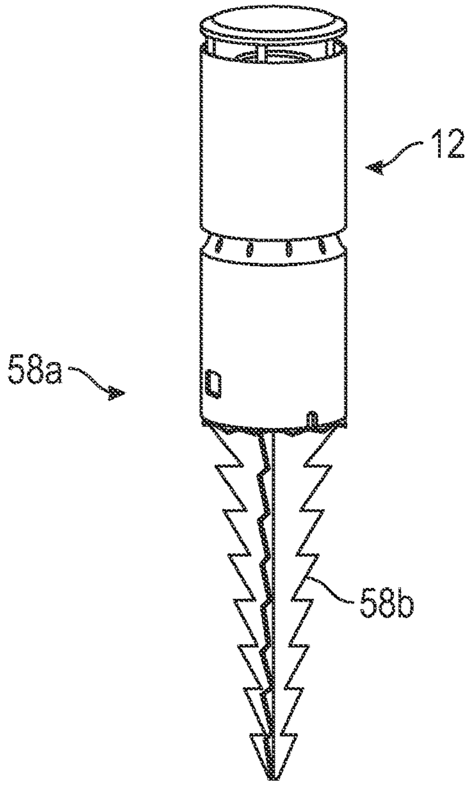
FIG. 9B is a perspective view of a ground spike mounting structure coupled to the insect repeller station of FIG. 3A.
Figure 9C:
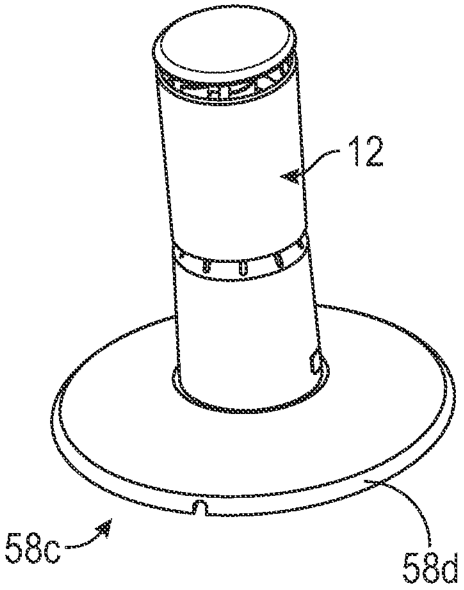
FIG. 9C is a perspective view of a pedestal mount coupled to the insect repeller station of FIG. 3A.
Figure 9D:
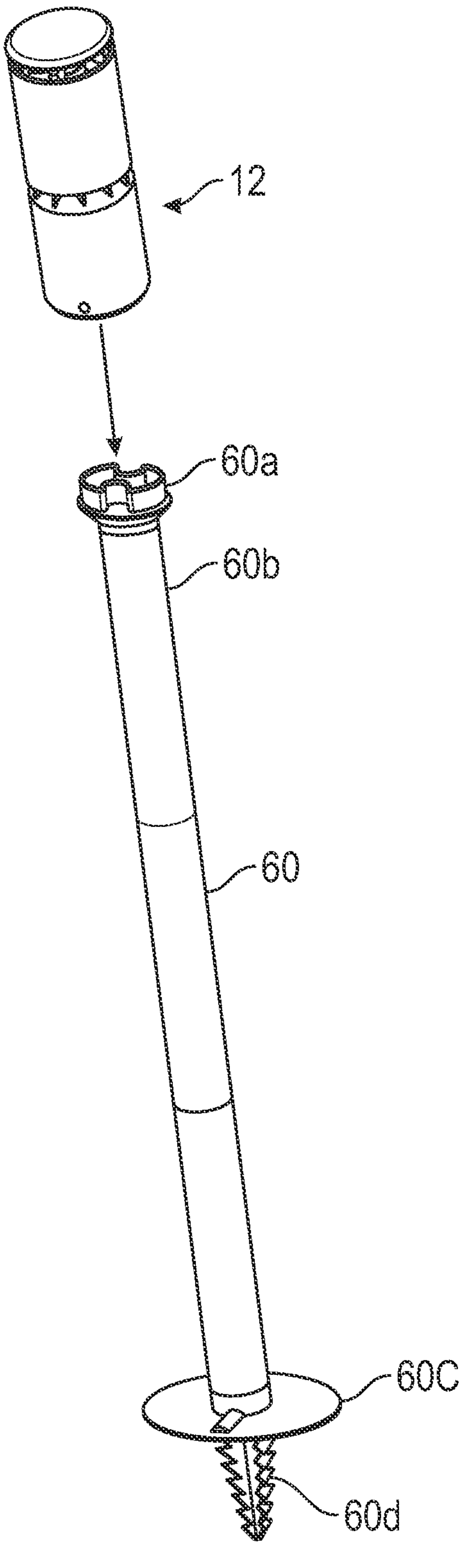
FIG. 9D is an exploded, perspective view of a pole mount coupled to the insect repeller station of FIG. 3A.

Referring now to FIGS. 9A-9D, the insect repeller station accepts a wide variety of mounting and support bases. These bases provide various mounting and location options so that the linked stations may be placed in preferred locations within the target insect control area. FIG. 9A illustrates an embodiment of a wall or flat surface mount 56. The wall mount 56 may include an integrally-formed interface structure similar to mounting interface 18*a* or may accept attachment of the mounting interface 18*a*. FIG. 9B illustrates an embodiment of a low level or ground mount 58*a* that includes a spike 58*b* permitting insertion into soil, mulch or other landscape materials. As shown in FIG. 9C, a surface mount 58*c* includes a pedestal or stabilizing plate 58*d* to prevent tipping on flat, hard surfaces. In an alternative arrangement, the stabilizing plate 58*d* may be provided in conjunction with the spike 58*b* to further stabilize the station on soft ground. FIG. 9D illustrates an elevated mount or mounting post 60 to provide elevated positioning of the repeller station above the ground. In the illustrated embodiment, the mounting post 60 includes a mounting head 60*a* similar to mounting interface 18*a* and at least one post section 60*b*. The post sections may be connected together by any suitable method, such as snaps, threads, interference or slip fit interfaces, and the like. Alternatively, the post section may be configured as a single piece structure or may be telescoping sections. A stabilizing plate 60*c* including a spike 60*d*, similar to plate 58*d*, may be provided if desired or the spike alone may be used.

Figure 10A:
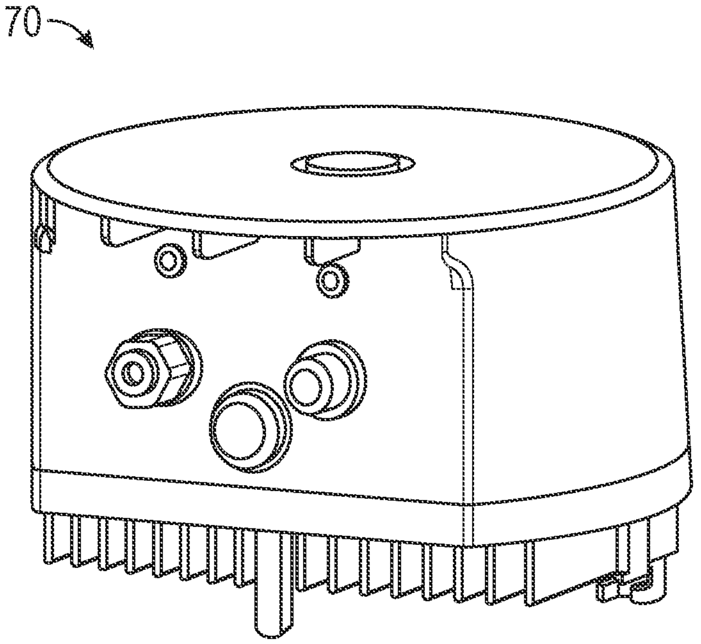
FIG. 10A is a front, perspective view of a controller hub of the linked insect repeller system of FIG. 2.
Figure 10B:
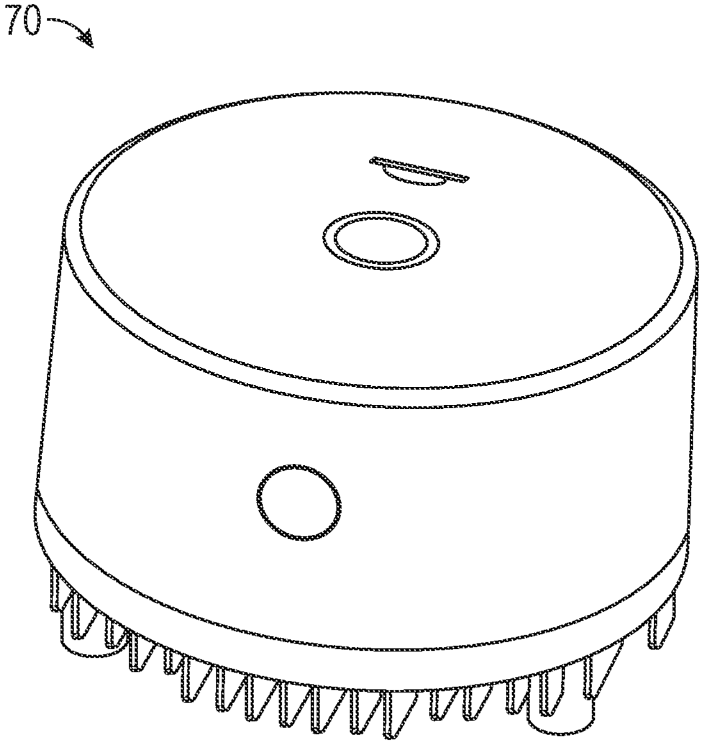
FIG. 10B is a rear, perspective view of the controller hub of the linked insect repeller system of FIG. 8B.
Figure 10C:
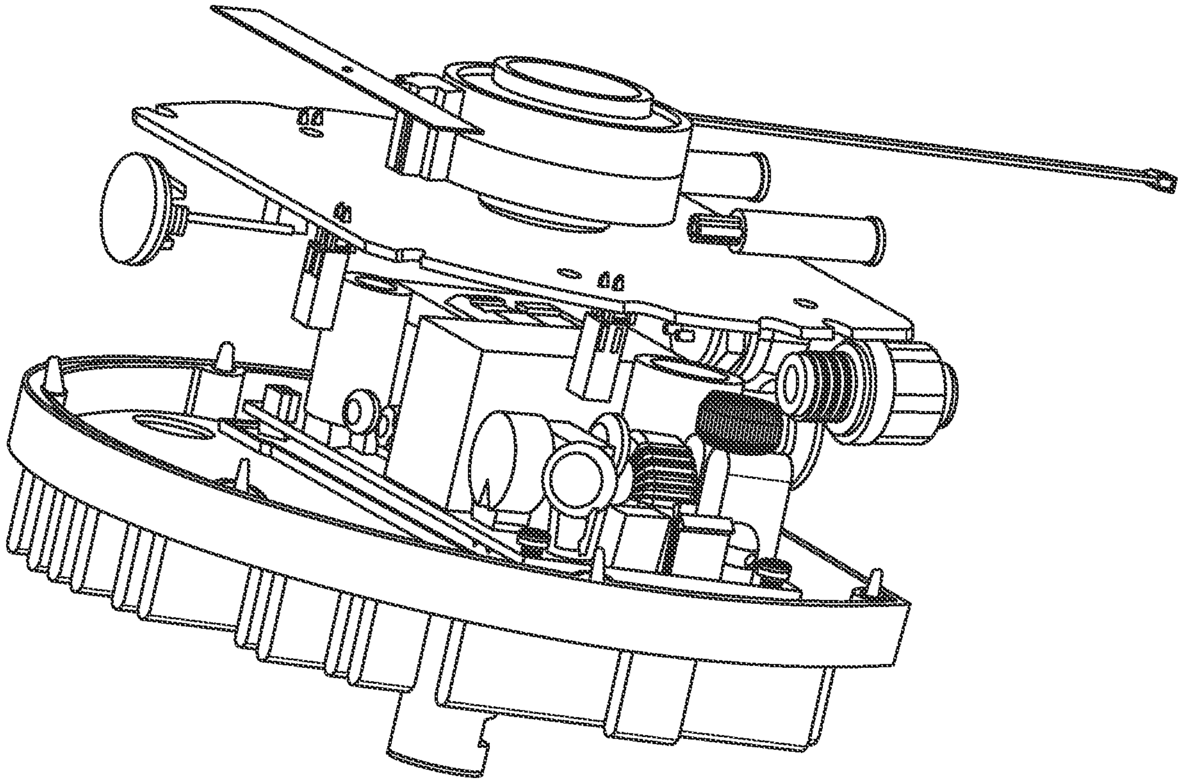
FIG. 10C is a rear, perspective view of the controller hub of FIG. 8B with the housing cover removed.

Referring now to FIGS. 10A-10C, there is illustrated an embodiment of a hub controller, shown generally at 70. The hub controller 70 provides a power source and control of the linked repeller stations as described above. The hub controller may be a separate structure or integrated into one or all of the repeller stations 12. The hub controller 70 may be configured as a timer to energize and de-energize the repeller stations in response to a user time input, or as a photo-sensor or electronic eye to energize the station or stations in response to outdoor light changes, or as a manual on/off switch.

In another embodiment, the hub controller executes a control algorithm that energizes the heating element of one or more of the linked repeller stations in response to certain inputs indicative of insect volume and intensity, termed insect pressure. In one embodiment, the target insects are predominantly mosquitos and the control inputs are factors associated with mosquito presence. Certain inputs are based on transient conditions, such as predicted weather events and patterns, other inputs are based on geography, such as proximity to bodies of water and certain topographies that may promote mosquitos. Examples of some transient condition input parameters are time of year, wind speed, temperature, humidity, precipitation—amount over time. These transient inputs may be accessed from web-based providers of weather-related data or may be acquired on site through weather measurement instrumentation. Examples of geography input factors are location coordinates, elevation, mapped topographies of standing water, and manually inputted factors for specific localized conditions.

The controller determines mosquito or insect pressure based on selected parameters known to promote or have an increased probability of mosquito populations. The controller powers the heater assembly which vaporizes a known volume of repellent material over a specific time period. This provides a material density factor for a given area such that the output provides a desired level of insect control. In forced convection embodiments of the repeller station, the fan may be pulsed to provide additional material to counteract conditions that inhibit the target treatment area maintaining a desired material density. In one embodiment, the hub controller may include different heating schedules for use with different insect chemicals for a variety of purposes. As an example, metofluthrin may be used to repel mosquitos in all or a few of the repeller stations. Other stations may include repellent materials that target other insects or animals (such as dogs, cats, deer, skunks, etc.). The hub controller may operate each station differently depending on the type of fluid and the location of the station relative to the environment. Alternatively, the fluid in one or more of the stations may be formulated to attract certain desirable wildlife, such as hummingbirds, butterflies, and the like if so desired.

In one operational arrangement, the controller 70 operates the heating element 26 using a closed loop control algorithm to operate the electric heater 26 to volatize the repellent fluid in a substrate, illustrated as the wick 24. The heater 26 is cycled to create a heated zone around the wick at one or more temperature profiles matched to one or more repellent formulas. In the closed-loop control system, power to the heater is regulated based on a relationship between the temperature sensor output, and proximity to a target temperature. If the temperature sensor output is below a lower threshold, power is applied to the heater until an upper threshold is met, at which point the heater is de-powered. The heater will begin to cool once depowered, and will again receive power when the lower threshold is met. This cycle continues and creates a steady and consistent temperature in between the upper and lower threshold setpoints. These upper and lower temperature thresholds bound the operating temperature of the heater. Modifying the upper and lower temperature thresholds permits movement of the operating temperature of the repeller station up and down. The varying thresholds permit different volatilizable materials to be used in the same repeller station. The thresholds may further be varied to tune performance of the system, either locally or remotely. In certain embodiments, the temperature setpoints can trigger notifications regarding performance and diagnostics. In one example, when a higher than usual temperature threshold is crossed, the controller may trigger a fault notification and/or disable the repeller.

In certain embodiments, the evaporator bottle may include a chip or other data source to indicate the type of fluid present, and other information such as bottle volume, capillary substrate material or porosity, that may change or direct the heater cycling and temperature profile. The chip may communicate through contacts in the mounting apertures or detents 50*a* in the hood 50 that communicate through mating contacts in the engage the attachment bosses 54 of the heater housing. A temperature sensor, for example a negative temperature coefficient (NTC) thermistor, to determine the temperature of the heater body that is used in a feedback loop to regulate power to the heater to achieve a target temperature level. Alternatively, the temperature sensor may be a positive temperature coefficient (PTC) thermistor used in conjunction with an open loop control system to create a similar temperature profile.

The hub controller 70 may further include an analog antenna and a Wi-Fi® wireless local area networking enabled antenna to provide communication with information sources for various inputs to the control algorithm. These inputs may include remote control access to provide operational functionality from a remote control, smart phone, computer or similar device. The hub controller may include a single antenna or multiple antennas for any type of communication desired. Operational parameters and usage data may be communicated to a remote display showing repeller operating status, material fill level, lighting status, and operating schedule, among other data. The hub controller may also include a manual override or manual discharge intensity feature to permit operation without use of transient and geographical inputs, if so desired. The hub controller may further provide an aesthetic output to the repeller stations in the form of light array operation. The light bar system may be adjusted to a desired color for entertainment purposes and may be coordinated with an audio component. The light operation may also be indicative of the operational state of the device indicating power on, low fluid level, specific unit operation or any other information concerning the status of the device.

As disclosed above in an alternative embodiment, the control features and/or the power feature of the hub controller may be integrated into one or more of the repeller stations permitting a single unit to operate independently or operate a plurality of stations. The stations 12 may each communicate, either through a wired connection or wirelessly, and provide a self-address function upon start-up and report individual station operating parameters during operation for performance monitoring, troubleshooting, and analytics. In yet another embodiment of the repeller system, the unit may include a sensor embedded in the reservoir bottle or mounting hood that conveys information regarding the type of repeller material in the bottle, an appropriate heating cycle and/or heating parameters to vaporize the contents, the amount of material in the bottle, and/or the manufacturer of the bottle and contents.

The principle and mode of operation of this invention have been explained and illustrated in its preferred embodiment. However, it must be understood that this invention may be practiced otherwise than as specifically explained and illustrated without departing from its spirit or scope.

What is claimed is:

1. An insect repeller station comprising:

an upper section defining an interior volume;

a heating element supported in a housing and including an aperture, the housing extending from a support arm into the interior volume of the upper section, the housing including a bottle support structure configured as opposing bosses extending from the housing; and a fluid bottle including a bottle attachment point, a reservoir, and a wick, the bottle attachment point configured as a hood partially surrounding the wick and having opposed detents that engage the attachment bosses to form a snap fit engagement with the bottle support structure to secure the fluid bottle to the housing, a portion of the hood contacting the housing to align the wick through the aperture in a generally concentric orientation within the heating element, the reservoir positioned adjacent to the support arm.

2. The insect repeller station of claim 1 wherein the support arm is connected to a lower section of the insect repeller station and cantilevered into the interior volume, the support arm housing electrical and/or communication connections to the heating element.

3. The insect repeller station of claim 1 wherein the hood includes an outer attachment structure configured to interface with a bottle lid, the bottle lid configured to enclose the wick and contain fluid contents of the reservoir.

4. The insect repeller system of claim 1 wherein one of the support arm or the housing is includes a fluid level detection device configured to measure and report a fluid level of fluid contents of the reservoir to a controller.

5. The insect repeller station of claim 4 wherein the fluid level detection device is configured to measure and monitor a bottle weight by one of a load cell, a strain gauge, or a weight scale.

6. The insect repeller station of claim 4 wherein the controller is configured to generate a signal proportional to the fluid level.

7. The insect repeller station of claim 1 wherein the hood forms a semicircular section around the wick and includes an open section that the housing passes through.

8. The insect repeller station of claim 1 wherein the fluid bottle includes a reservoir cap and a bottle lid, the reservoir cap having a venting structure to prevent vacuum formation within the reservoir as fluid contents are drawn by the wick, and the bottle lid forms a seal with the vent to contain the fluid contents.

9. The insect repeller station of claim 1 wherein the fluid bottle includes a reservoir cap having a venting structure to prevent vacuum formation within the reservoir as fluid contents is drawn by the wick, and a removable vent closure seals the vent to contain the fluid contents.

* * * * *